(12) United States Patent
Badawi et al.

(10) Patent No.: US 9,632,187 B2
(45) Date of Patent: Apr. 25, 2017

(54) MODULAR POSITRON EMISSION TOMOGRAPHY KIT

(71) Applicant: The Regents of the University of California, Oakland, CA (US)

(72) Inventors: Ramsey D. Badawi, Sacramento, CA (US); Simon Cherry, Davis, CA (US); Felipe Godinez, Davis, CA (US); Jonathan Poon, Davis, CA (US); Martin Judenhofer, Davis, CA (US); Jinyi Qi, Davis, CA (US); Abhijit Chaudhari, Sacramento, CA (US); Madagama Sumanasena, Sacramento, CA (US); Julien Bec, Davis, CA (US)

(73) Assignee: The Regents of the University of California, Oakland, CA (US)

(*) Notice: Subject to any disclaimer, the term of this patent is extended or adjusted under 35 U.S.C. 154(b) by 157 days.

(21) Appl. No.: 14/303,282

(22) Filed: Jun. 12, 2014

(65) Prior Publication Data
US 2014/0367577 A1    Dec. 18, 2014

Related U.S. Application Data

(60) Provisional application No. 61/834,256, filed on Jun. 12, 2013, provisional application No. 61/919,649, (Continued)

(51) Int. Cl.
*G01T 1/202* (2006.01)
*G01T 1/29* (2006.01)
(Continued)

(52) U.S. Cl.
CPC ............ *G01T 1/2985* (2013.01); *A61B 6/037* (2013.01); *A61B 6/4411* (2013.01); *A61B 6/508* (2013.01); *Y10T 29/49117* (2015.01)

(58) Field of Classification Search
USPC ...... 250/336.1, 363.03, 363.04, 363.08, 366, 250/370.1, 361 R
See application file for complete search history.

(56) References Cited

U.S. PATENT DOCUMENTS

| | | | |
|---|---|---|---|
| 2005/0151087 A1* | 7/2005 | Ueno | G01T 1/2928 250/370.09 |
| 2011/0297840 A1* | 12/2011 | Tanaka | A61B 6/032 250/393 |
| 2015/0028218 A1* | 1/2015 | Kataoka | G01T 1/1644 250/367 |

* cited by examiner

*Primary Examiner* — David Porta
*Assistant Examiner* — Carolyn Igyarto
(74) *Attorney, Agent, or Firm* — Kilpatrick Townsend & Stockton LLP

(57) ABSTRACT

Systems and methods for a positron emission tomography (PET) kit are described. A PET detector kit may include a gantry, a plurality of PET detector modules, and an event processing device. A PET detector module may include a housing, a crystal, a light detector, and a communication component. The housing may include at least one connective element configured to removably and adjustably couple the PET detector module to the gantry. The crystal may be located within the housing. The light detector may be configured to detect light emitted by the crystal. The communication component may be configured to communicate data from the at least one light detector to an event processing device. The event processing device may receive data from the plurality of PET detector modules and may cause the one or more processors to determine coincidence events based on the received data.

21 Claims, 20 Drawing Sheets

Related U.S. Application Data filed on Dec. 20, 2013, provisional application No. 61/919,652, filed on Dec. 20, 2013.

(51) Int. Cl.
*A61B 6/03* (2006.01)
*A61B 6/00* (2006.01)

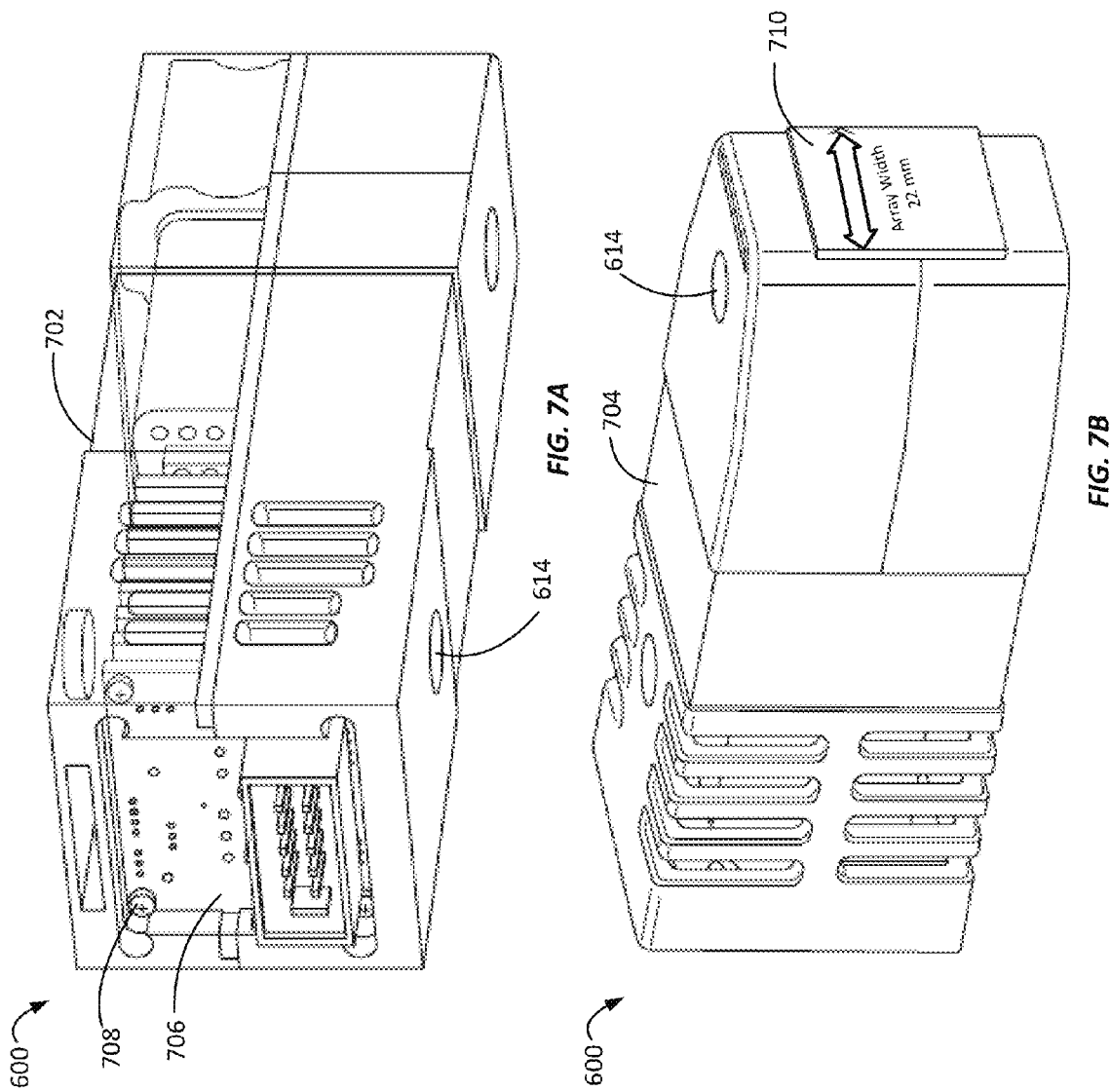

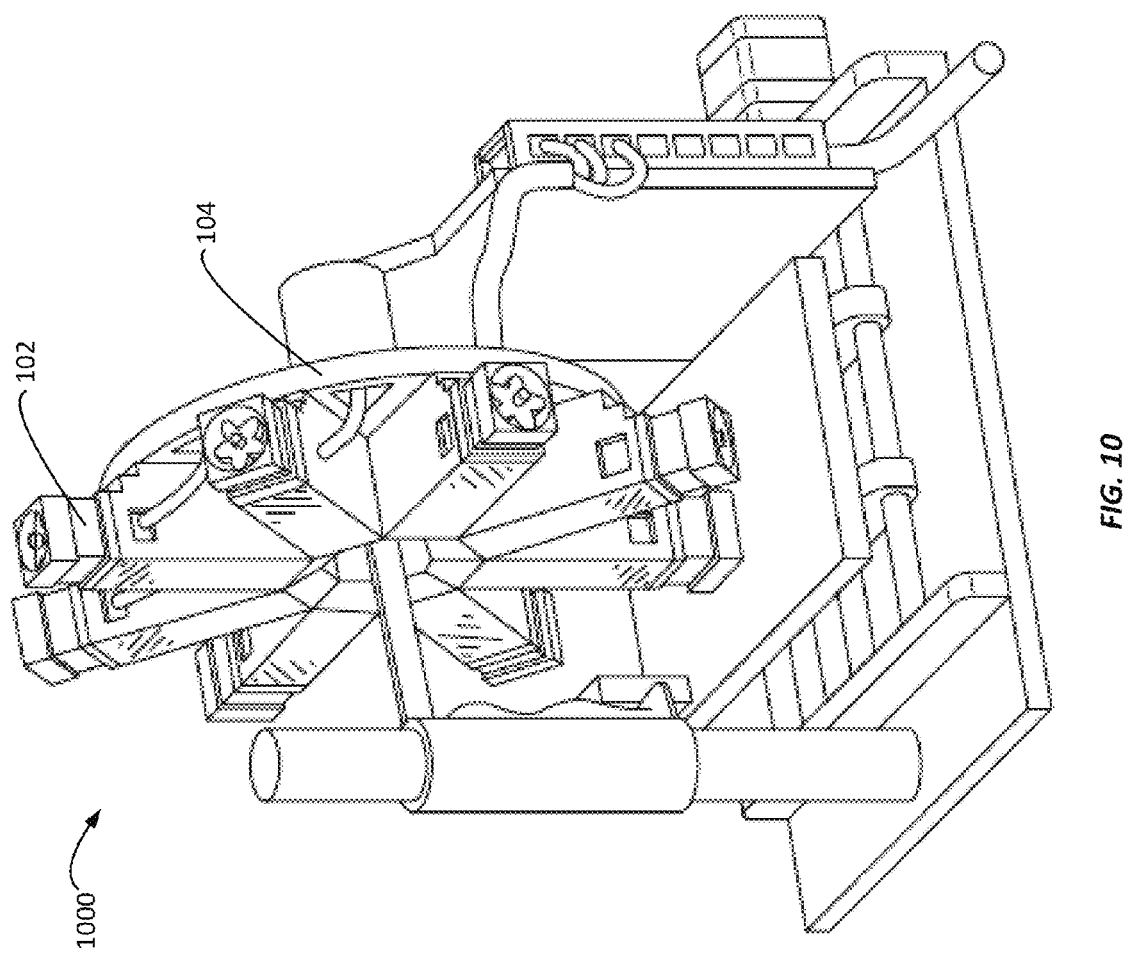

MODULAR POSITRON EMISSION TOMOGRAPHY KIT

STATEMENT AS TO RIGHTS TO INVENTIONS MADE UNDER FEDERALLY SPONSORED RESEARCH AND DEVELOPMENT

This invention was made with Government support under Grant Nos. CA129561 and 170874, awarded by the National Institutes of Health. The Government has certain rights in this invention.

CROSS-REFERENCE TO RELATED APPLICATIONS

This application is a non-provisional application of provisional patent application 61/834,256, entitled, "Modular Positron Emission Tomography Kit," filed Jun. 12, 2013; provisional patent application 61/919,649, entitled, "Positron Emission Tomography Kit with Wireless Detectors," filed Dec. 20, 2013; and provisional patent application 61/919,652, entitled, "Positron Emission Tomography Detector Module Case and Skin," filed Dec. 20, 2013; the disclosures of which are incorporated by reference herein in their entirety.

BACKGROUND

Position emission tomography (PET) is an imaging technology used for medical procedures and research. Scanning performed with a PET system can be used produce images of specimens, such as two-dimensional and three-dimensional images of organisms. PET imaging can be used to track the movement of matter through an organism.

Prior to PET imaging, a tracer may be injected into, ingested by, or otherwise inserted into a specimen. The tracer may be a radioactive contrast agent, such as $^{18}$F-fluorodeoxyglucose (FDG). FDG is a glucose analog that is internalized more rapidly by cancer cells than by normal cells. As the FDG travels through the specimen (e.g., the specimen's circulatory system), the FDG can be monitored by the PET scanner. In some embodiments, the FDG may travel to an area of interest in the specimen. For example, the FDG may adhere to or be taken up by cells of interest. The high level of radioactivity of the area of interest in comparison with other tissue can allow visualization of an area of interest as a PET image based on a PET scan. Various tracer types, such as RGD peptides, nitroimidazoles, Cu-ATSM, etc., may be selected for a range of imaging applications, such as identifying hypoxia in tissues, imaging organs, tracing the flow of blood or other compounds through an organism, etc.

After the tracer has entered the organism, a PET scanner can detect pairs of annihilation photons emitted by the tracer isotope. Typically, one or more pairs of PET detectors are used to detect pairs of emitted protons. A specimen may be positioned between two PET detectors.

As the tracer in the specimen decays, the isotope emits a positron. When the positron interacts with an electron, a pair of annihilation photons is produced, with the photons moving in opposite directions. The two photons can be detected by two PET detectors that are located across from each other with respect to the specimen. When the two photons reach crystals of the two PET detectors, the crystals can absorb the energy of the photons and emit the energy as light. One or more light detectors attached to a crystal can determine the position and time of arrival of the photon (i.e., an event) based on light emitted by the crystal. If two light detectors of the two PET detectors detect corresponding photon arrivals within a particular time frame, the photons may be determined to be a coincidence event (and therefore are highly likely to have originated from the same annihilation event). Alternative PET scanning systems may use solid state detectors and gas detectors in lieu of crystals for detecting photon arrivals.

Images may be constructed from the data acquired by the PET imaging system. For example, mathematical construction, e.g., maximum a posteriori (MAP) reconstruction, can be used to construct an image based on the distribution of activity detected by the PET detectors. The detectors may be configured to detect one or more of beta rays, gamma rays, and other high energy radiation.

Currently available PET scanners may be unable to image or suboptimal for imaging certain conditions and features, such as features that are small compared to spatial resolution of whole-body PET scanners. The size ranges of available PET scanners do not accommodate all potential imaging subjects of interest to researchers and health practitioners. PET scanners designed to have a fixed configuration may limit the applications for which PET scanning can be performed. Additionally, the structures of current PET scanners limit the settings in which PET scanners are operated.

Embodiments described herein address these and other problems, individually and collectively.

BRIEF SUMMARY

A positron emission tomography (PET) module, modular PET system, and method are described.

One embodiment is directed to a PET detector module for connection to a gantry. The PET detector module may include a housing, a crystal, a light detector, and a communication component. The housing may include at least one connective element configured to removably and adjustably couple the PET detector module to the gantry. The crystal may be located within the housing. The light detector may be configured to detect light emitted by the crystal. The communication component may be configured to communicate data from the at least one light detector to an event processing device.

Another embodiment is directed to a PET detector kit. The kit may include a gantry, a plurality of PET detector modules, and an event processing device. A PET detector module may include a housing, a crystal, a light detector, and a communication component. The housing may include at least one connective element configured to removably and adjustably couple the PET detector module to the gantry. The crystal may be located within the housing. The light detector may be configured to detect light emitted by the crystal. The communication component may be configured to communicate data from the at least one light detector to an event processing device. The event processing device may include a processor and one or more non-transitory computer readable storage media. The computer readable storage media may contain instructions. The instructions may cause the processor to receive data from the plurality of PET detector modules. Additionally, the instructions may cause the processor to determine coincidence events based on the received data.

A further embodiment is directed to a method. The method may include coupling a PET detector module to a gantry. At least one connective element may be used for the coupling of the PET detector module to the gantry. The PET detector module may include a housing, a crystal, a light detector, and a communication component. The housing may include at least one connective element. The crystal may be located within the housing. The light detector may be configured to detect light emitted by the crystal. The communication component may be configured to communicate data from at least one light detector to an event processing device. A position of the PET detector module relative to the gantry may be adjusted. The position may be adjusted using the at least one connective element. The PET detector module may be decoupled from the gantry.

These and other embodiments are described in further detail below.

BRIEF DESCRIPTION OF THE DRAWINGS

FIGS. 7A-B show additional perspective views of a case for a PET detector module.

FIG. 10 shows an illustrative PET scanner system assembled from a modular PET kit, according to a first embodiment.

DETAILED DESCRIPTION

Figure 1:
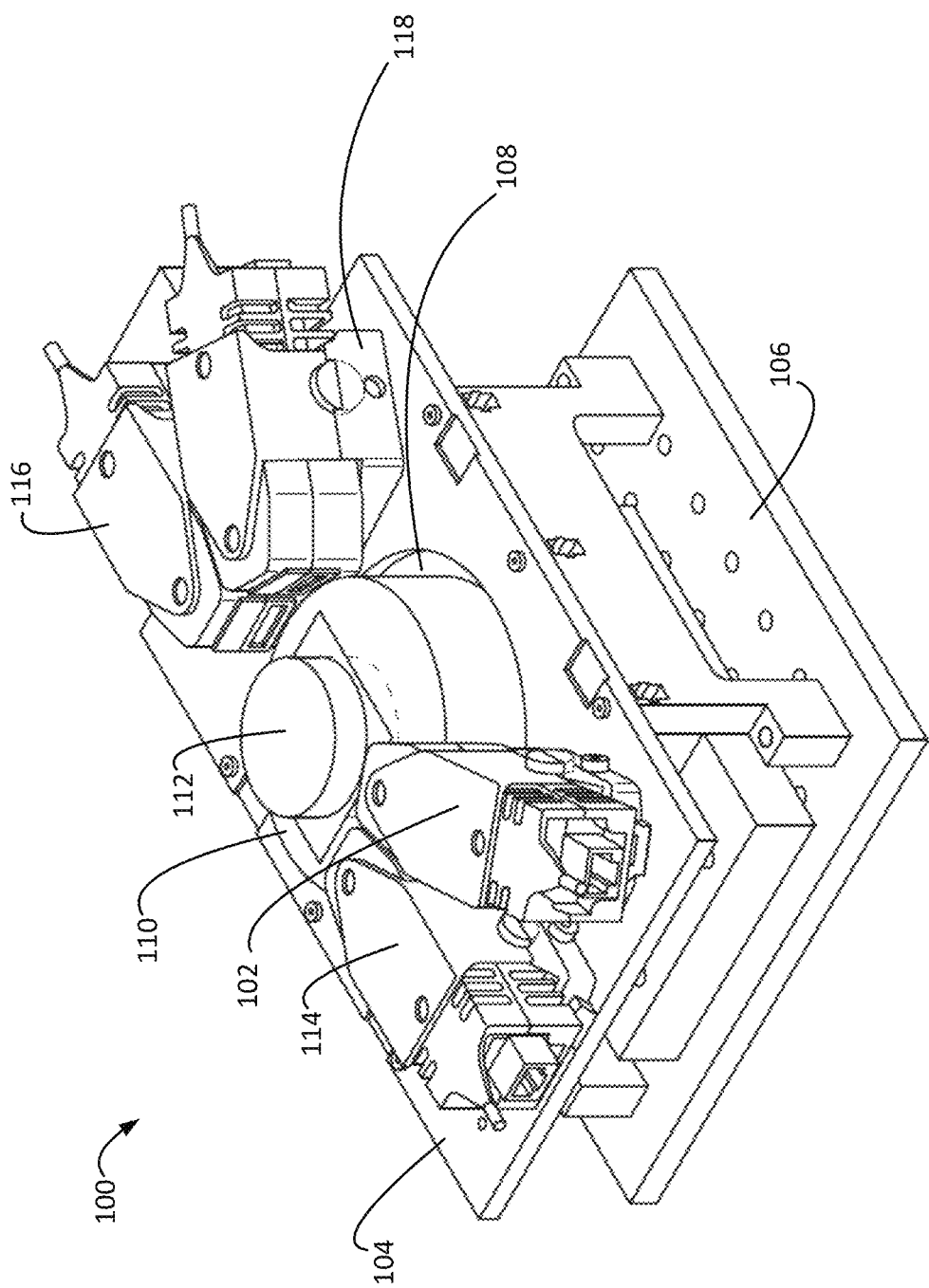
FIG. 1 shows an illustrative PET scanner, according to an embodiment.

Systems and methods related to a kit for assembling a positron emission tomography (PET) scanner are disclosed.

A modular PET kit may include hardware and software components that allow a PET scanner to be assembled in various configurations. In this manner, the modular PET kit can be adaptable to various clinical and research objectives.

A modular PET kit may include a plurality of PET detector modules. Each PET detector module may be capable of detecting photons emitted by a tracer isotope in a specimen to be imaged. The PET detector modules may be attached to a variety of gantry structures. In some embodiments, the modular PET kit can include multiple gantries. It may be desirable to custom fabricate a gantry for use with the PET detector modules for a particular research or clinical application.

The PET detector modules can include connective elements for attaching the PET detector modules to a gantry. The connective elements may allow the PET detector modules to be removable from the gantry and/or adjustable with respect to the gantry. For example, the connective elements may allow the PET detector modules to be removed from the gantry and/or adjusted with respect to the gantry without requiring the use of any tools.

A PET detector module can include a communication component for communicating data collected by the PET detector module to a processing system. The processing system can include one or more computers for determining coincidence events and constructing images based on the determined events.

The modular PET kit can be flexible and scalable, allowing it to be optimized for a variety of imaging subjects including small specimens (e.g., mouse brain), medium-sized animals too large to fit in currently available small animal scanners (e.g., rabbit, dog, non-human primate), humans and portions of humans (e.g., limbs, the neck), large specimens, and specimens requiring a specialized geometry (e.g., to image subjects in various positions, to image specific parts of an subject, to protect the PET kit components from movement of subjects, etc.). For example, a modular PET kit can be used to construct a scanner that can image the limb of a standing horse while protecting the PET kit components from the horse.

Because the modular PET kit is adaptable to various configurations, scanners built from the modular PET kit can be used in a variety of settings, such as in an operation room, interventional radiology suite, and outdoors. PET imaging in the operating room could be used for applications such as active node location, assessment of excision boundaries in oncology, and PET guided biopsy.

The modular PET kit may provide high resolution imaging, allowing study of subjects that are small relative to the resolution of whole-body PET scanners. For example, a PET scanner constructed from the modular PET kit may be used for study of vascular pathologies of the extremities, such as imaging blood vessels in the human foot and neck. Additionally, the modular PET kit can be used to build a scanner for quantifying inflammation, such as inflammatory arthridities. The scanner may be capable of distinguishing inflammation from muscle uptake in bellwether organs such as the wrist. Additional imaging applications for the modular PET kit include imaging of small animal limbs and paws, such as imaging of the mouse paw.

PET Scanner Assembled from Modular Kit

FIG. 1 shows an illustrative PET scanner 100 assembled from a modular PET kit, according to an embodiment. PET scanner 100 includes a plurality of PET detector modules 102. PET detector modules 102 may be coupled to gantry 104. Gantry 104 may be any structure to which PET detector modules may be mounted.

In the illustrative example of FIG. 1, gantry 104 is a table. Gantry 104 is shown mounted to a lab bench 106, however it will be recognized that gantry 104 may be a self-supporting structure. The table may include opening 108 through which specimen table 110 may pass. Specimen 112 may be placed on specimen table 110. In some embodiments, specimen table 110 may be motorized such that specimen table 110 is caused to rotate and/or translate by one or more motors. Specimen 112 may be caused to move by the movement of specimen table 110. In various embodiments, PET detector modules 102 may rotate and/or translate relative to a static specimen. For example, PET detector modules may be mounted on an element of gantry 104 that is motorized such that the element is caused to rotate and/or translate by a motor.

Typically, a specimen is located between a pair of PET detector modules. For example, specimen 112 may be located between individual PET detector modules 114 and 116. A PET detector may be paired with multiple other PET detectors for imaging specimen 112. For example, detector 116 may be paired with detectors 114 and 102 for imaging specimen 112.

PET detector modules 102 may be coupled to gantry 104 via connective elements 118. In some embodiments, PET detector modules are removably coupled to gantry 104. In this manner, PET detector modules 102 can be connected to gantry 104 and subsequently removed from gantry 104. PET detector modules 102 may be adjustably connected to gantry 104. For example, PET detector modules 102 may be adjusted to be closer to or further away from specimen 106. PET detector modules 102 may be adjustable relative to gantry 104 with one, two, or more degrees of freedom. In some embodiments, PET detector modules 102 may be adjusted relative to gantry 104 without disconnecting PET detector module 102 from gantry 104 or with minimal disruption of the connection between PET detector module 102 and gantry 104.

Figure 2:
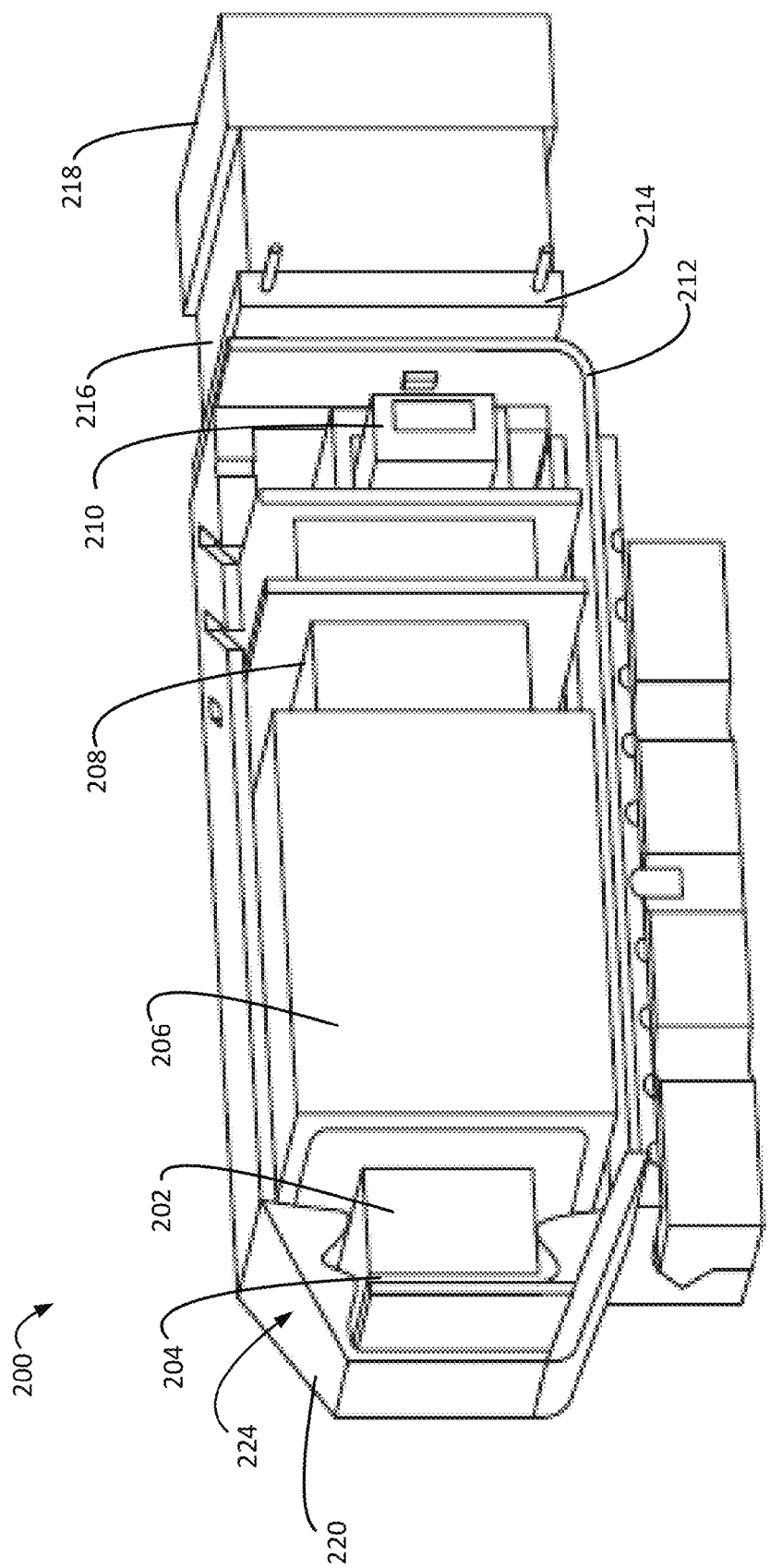
FIG. 2 shows an illustrative PET detector module, according to a first embodiment.
Figure 3:
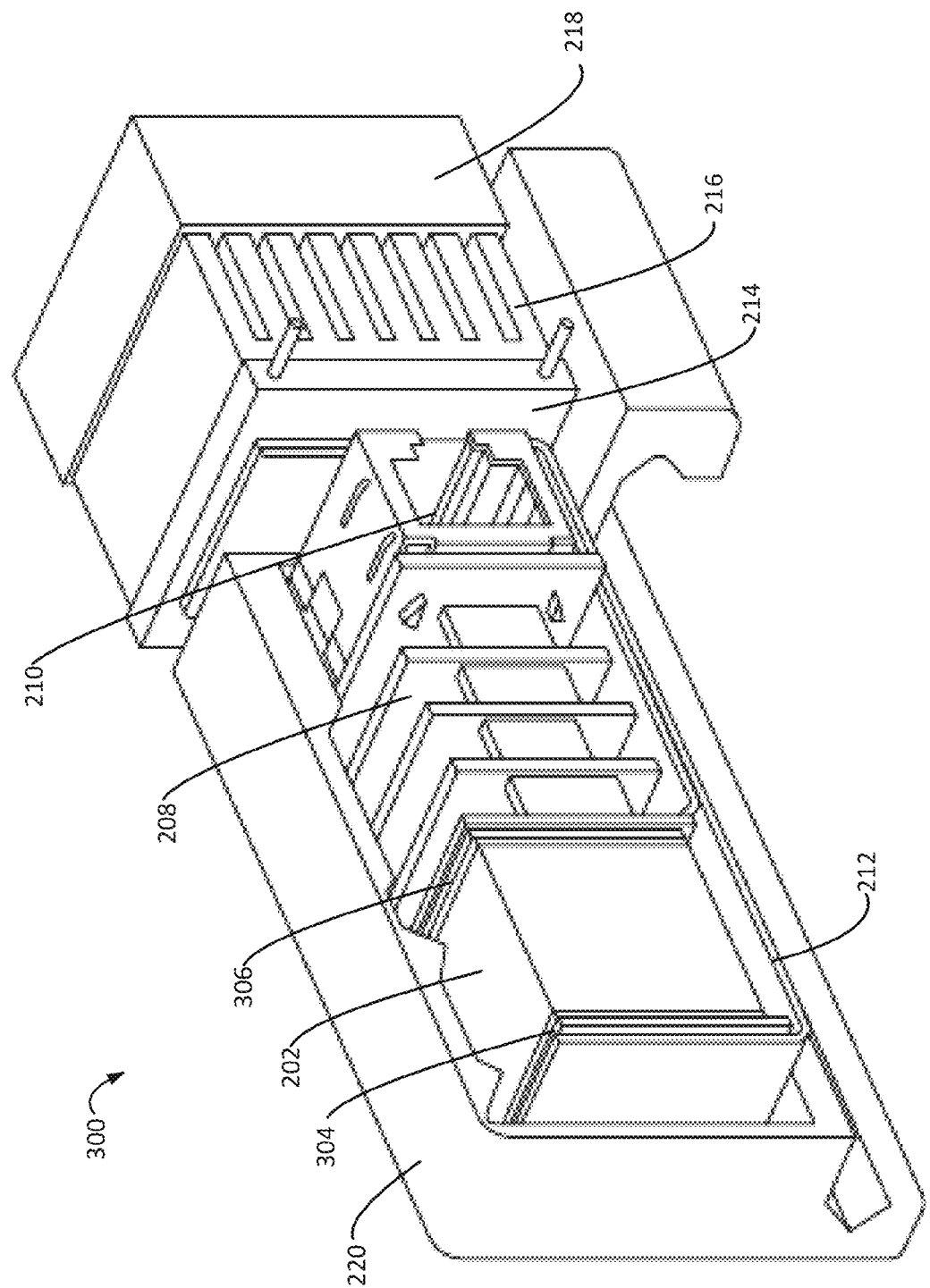
FIG. 3 shows an illustrative PET detector module, according to a second embodiment.
Figure 4:
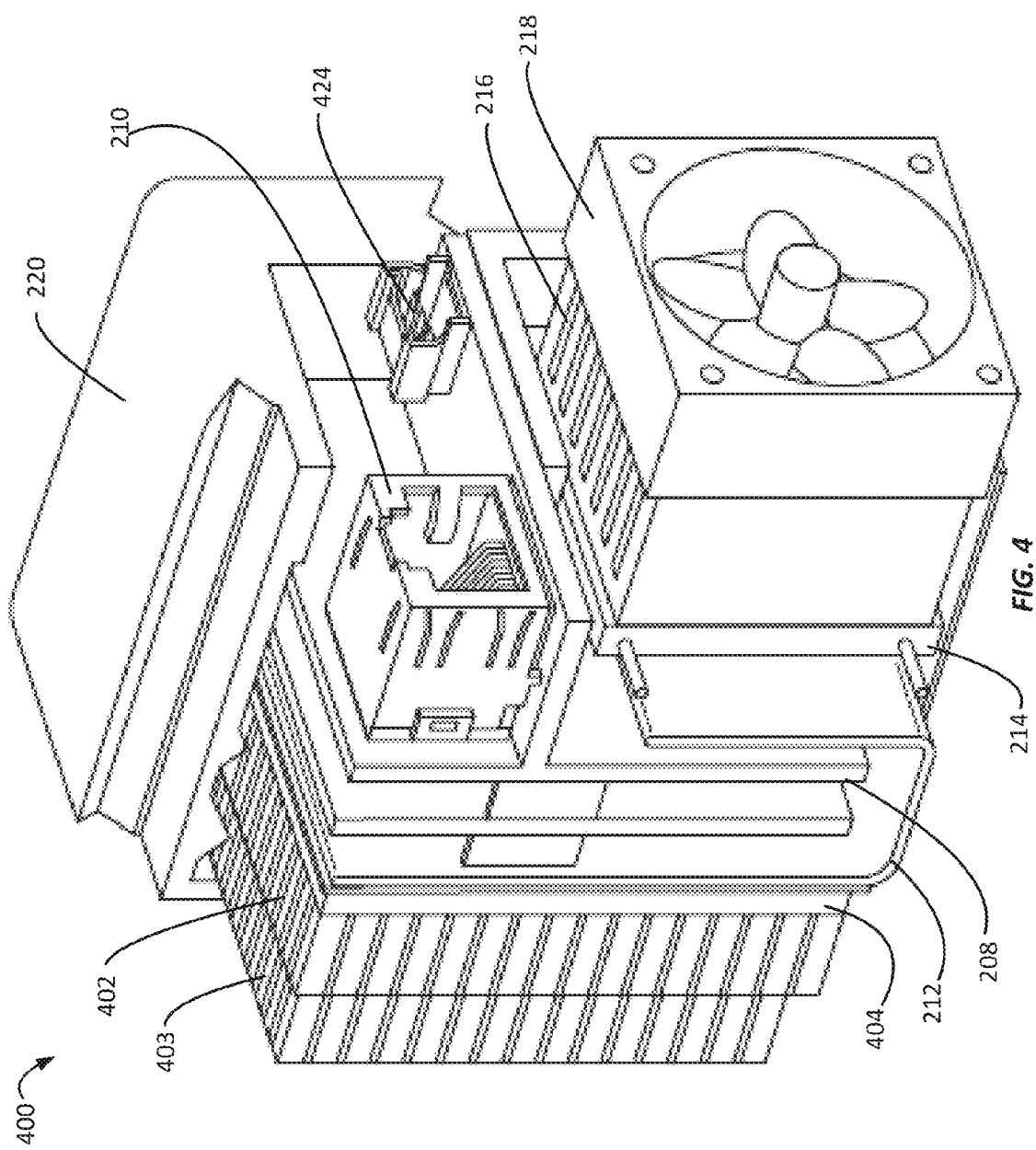
FIG. 4 shows an illustrative PET detector module, according to a third embodiment.

The components and layout of a PET detector module 102 may vary depending on factors such as a target imaging resolution, specimen size, geometry in which the PET detector module 102 will be arranged, target cost, etc. FIGS. 2-4 show various configurations for PET detector modules, according to embodiments. PET detector module 102, described above with regard to FIG. 1, may be a PET detector module 200, 300 or 400 as described below with regard to FIGS. 2, 3 and 4, respectively. Any of the components described with regard to PET detector modules 200, 300, or 400 may be used within PET detector module 102.

PET Detector Module

FIG. 2 shows an illustrative PET detector module 200, according to an embodiment. PET detector module 200 may include crystal 202; light detectors 204, 206; one or more pre-amplifiers 208; communication component 210; heat control module elements 212, 214, 216 and 218; and housing 220. The components and configurations of PET detector module 300 and 400 may be components and configurations described with regard to PET detector module 200.

Crystal 202 may be a scintillating crystal, an array of scintillating crystals, a ceramic scintillator, or other material able to convert absorbed ionizing radiation energy into photons. Crystal 202 may include crystal material such as LYSO (Cerium-doped Lutetium Yttrium Orthosilicate $Lu_{2(1-x)}Y_{2x}SiO_5$), BGO (Bismuth germinate $Bi_4Ge_3O_{12}$), GSO (Gadolinium Orthosilicate $Gd_2SiO_5$), LSO (luterium oxyorthosilicate $Lu_2SiO_5$) MLS, LGSO, or other crystal material. A crystal array may have, e.g., 7×7 elements, 10×10 elements, 14×14 elements, 16×16 elements, 20×20 elements, 36×36 elements, or another configuration of elements. Crystal 202 may be a rectangular prism or array of rectangular prisms. It will be recognized that other crystal shapes and arrangements of crystal arrays may be used. For example, crystal 202 may include one or more crystals with a square cross section, a hexagonal cross section, a triangular cross section, etc. A crystal array may be a triangular array of square elements, a triangular array of triangular elements, a hexagonal array of elements, etc. The crystal may have a thickness in the range of 1 mm to 30 mm, such as 8 mm to 10 mm, e.g., 8 mm. The crystal pitch may be in the range of 0.25 mm-6 mm, such as 0.5-1.0 mm, e.g., 0.5 mm. One or more surface treatments may be applied to crystal 202, such as polishing, etching, grinding, etc. In some embodiments, elements of a crystal array may be separated by a reflector. The reflector may be a white paper reflector, such as a Toray reflector (e.g., Lumirror®). Other reflectors may be used, such as Teflon®, enhanced specular reflection (ESR) film, barium sulphate powder, etc. A light guide may be used to spread light across the face of crystal 202.

In some embodiments, PET scanner system 100 may use a solid state detector and/or gas detector in lieu of crystal 202 for detecting photon arrivals. Where the term crystal is used herein, it will be understood that another type of photon detector, such as a solid state detector or gas detector, may be used.

In the exemplary embodiment of FIG. 2, PET detector module 200 may achieve spatial resolution close to the physical limits of PET. For example, PET detector module 200 may have spatial resolution in the range of 0.5 mm to 1.5 mm, such as 0.6 mm to 0.7 mm, e.g., 0.62 mm. For example, crystal 202 may be a crystal array with 36×36 elements. The crystal array may have a 0.5 mm crystal pitch. The crystal array may have a thickness in the range of 8 mm to 12 mm, such as 8 mm to 10 mm, e.g., 8 mm. The crystal array may have unpolished crystals and a white paper reflector, e.g., a Toray reflector. An exemplary imaging application for PET detector module 200 is imaging inflammation in the human finger.

PET detector module 200 may include at least one light detector. The at least one light detector may include one or more of a position sensing photomultiplier tube (PSPMT), a silicon photomultiplier (SiPM), an avalanche photodiode (APD), or other light detector. In some embodiments, the APD may be a position sensitive avalanche photodiode (PSAPD). A PSPMT may be, for example, a Hamamatsu M64 PSPMT. An SiPM may be a single SiPM or an SiPM array. Where the term SiPM array is used herein, it will be understood that a single SiPM may be used. An SiPM array may be, for example, a 4×4 element array of 3×3 $mm^2$ SiPM elements, such as SensL MicroFB-30035-SMT blue-sensitive SiPM elements. It will be understood that other array sizes (e.g., a 6×3 element array), sizes of SiPM elements (e.g., 2×2 $mm^2$, 6×6 $mm^2$, etc.), and types of SiPM elements may be used. In some embodiments, the SiPM array may be a monolithic array (i.e., an array manufactured from a single piece of silicon). An SiPM may be a position sensing SiPM. The APD, may be, for example, a large area APD manufactured by RMD.

In the illustrative example of FIG. 2, PET detector module 200 may include a first light detector, SiPM array 204, and a second light detector, PSPMT 206. Crystal 202 may be located between SiPM array 204 and PSPMT 206. For example, SiPM array 204 may be located adjacent to the face of crystal 202 that is proximate to the front face of PET detector module housing 220, e.g., the face of PET detector module housing that will be proximate to a specimen 112. SiPM array 204 may be coupled to crystal 202 via optical grease, an optical adhesive, or other coupling means. In some embodiments, a light guide may be located between SiPM array 204 and crystal 202. The light guide may be tapered or untapered. The light guide may have structures, such as cuts, for modifying light distribution. A coupling material such as optical grease, an optical adhesive, or other coupling material may be used to couple the SiPM array 204 to the light guide and to couple the light guide to crystal 202. PSPMT 206 may be located adjacent to the face of crystal 202 that is opposite to the face of crystal 202 to which SiPM array 204 is adjacent. In some embodiments, an APD may be used in lieu of SiPM array 204. In various embodiments, SiPMs may be preferable to APDs due to factors such as the comparatively greater cooling requirements of APDs and potential performance and reliability differences between APDs and SiPMs.

One or more light detectors may be used to determine x- and y-positions within crystal 202 where a photon is detected. An energy level may also be determined from the output of the one or more light detectors. A z-position within crystal 202 where a photon is detected may be determined from the output of the one or more light detectors. See FIG. 5 for an illustration of x-, y-, and z-axes relative to a crystal 202.

For each photon detection event, PET detector module 200 may produce event data including an x-position, a y-position, a z-position, an energy level, and a timestamp. In some embodiments, the x-position, y-position, and energy level may be determined from information detected by PSPMT 206. Alternatively, an x-position and y-position may be determined from information detected by multiple light detectors, such as PSPMT 206 and SiPM array 204. In another example, the x-position and y-position may be determined from information detected by two APDs located on opposite sides of crystal 202 or two SiPMs or SiPM arrays on opposite sides of crystal 202. A z-position may be determined from information from PSPMT 206 and SiPM array 204, from PSPMT 206 and an APD, or information from another component or combination of components. The timestamp may be determined from a clock component of PET detector module 200 or by a remote clock component, such as a clock component of a processing system.

PET detector module 200 may include one or more preamplifiers 208. Pre-amplifiers 208 may receive signals from light detectors, such as SiPM array 204 (or an APD) and PSPMT 206. Pre-amplifiers 208 may amplify the magnitude of the received signals. The amplified signals may be communicated from PET detector module 200 to a processing system. The processing system may include one or more computers configured to process event data, e.g., to determine coincidence events.

PET detector module 200 may include one or more communication components 210 for transmitting signals generated by light detectors to a processing system. The signals generated by light detectors may be amplified by pre-amplifiers 208 for transmission via communication component 210. Communication component 210 may include a communication port, such as an RJ-45 port. When a data cable is connected to the RJ-45 port and to the processing system, signals may be transmitted from PET detector module 200 to the processing system via the data cable. It will be recognized that other types of wired data connections and/or wired connection ports, e.g., USB, may be used.

In some embodiments, PET detector module 200 can communicate with a processing system via wireless communications, such as Wi-Fi communications. It will be recognized that other types of wireless communications, such as Bluetooth, cellular or other mobile communications, or combinations of wireless communications technologies, may be used. In some embodiments, a combination of wired and wireless communications technologies may be used for communication between PET detector module 200 and a processing system.

PET detector module 200 may include a heat control module. The heat control module may include a heat transfer device 212, a peltier 214, a heat sink 216, a fan 218, a temperature sensor, ventilation openings, a ventilation port, an airflow manifold and other heat control devices. Heat transfer device 212 may be a heat pipe. For example, heat transfer device 212 may be a micro heat pipe with acetone as a working fluid, such as a heat transfer device MHP-1220B by Amec Thermasol Ltd. Peltier 214 may be a peltier element that, in combination with other elements, such as heat transfer device 212, heat sink 216 and/or fan 218, may form a peltier cooler. In some embodiments, fan 218 may be detachable from PET detector module 200.

The speed of fan 218 may be controlled based on the output of a temperature sensor. For example, the speed of the fan may be increased when a signal output by the temperature sensor exceeds a threshold temperature. The speed of the fan may be decreased when a signal output by the temperature sensor falls below a threshold temperature. A threshold temperature may be determined based on heating tolerances of one or more components of PET detector module 200, such as an APD, a PSPMT, and/or an SiPM array. PET detector module 200 may include a processor, controller, or logic for controlling the speed of fan 218 based on input received from the temperature sensor. Alternatively, the output of the temperature sensor can be communicated to a processing system via communications component 210. A control signal for controlling fan 218 may be received by PET detector 200 from a processing system via communications component 210.

PET detector module 200 may include one or more power connectors (not shown). One or more power sources may provide power to one or more of light detectors 204, 206; pre-amplifiers 208, peltier 214, fan 218, and any other components that require power via the one or more power connectors. In some embodiments, a high voltage power connector and a low voltage power connector are provided. For example, an APD may require a high voltage power supply whereas an SiPM array may require a low voltage power supply. Multiple power connectors can be provided for detectors to accommodate the requirements of various components that may be included in the detector. PET detector module 200 may include a processor, controller, logic circuit, or other components for managing power distribution to various components of PET detector module 200. In some embodiments, a local power source, e.g., a battery, may be used to provide power to components of PET detector module 200 in lieu of power provided via the one or more power connectors.

PET detector module 200 may include a housing 220. Housing 220 may contain and/or hold in a fixed position one or more of crystal 202; light detectors 204, 206; pre-amplifiers 208; communication component 210; and heat control module elements 212, 214, 216 and 218. In some embodiments, housing 220 may partially or fully enclose the components of PET detector module 200 in a stable position such that the components are immobilized within housing 220. It may be necessary that one or more components of PET detector module 200 are precisely aligned with one another and/or with housing 220 for accurate sensing to occur. For example, it may be necessary for SiPM array 204 and PSPMT 206 to be aligned with crystal array 202. Further, it may be necessary for crystal array 202 to be precisely aligned with a visual reference on housing 202. Using housing 202 to hold the components of PET detector module 200 in fixed positions can allow PET detector module 200 to be transported, coupled to a gantry 104, adjusted relative to gantry 104, etc., while preventing or minimizing shifting of PET detector module components within housing 220.

Housing 220 may have openings to accommodate connections between components of PET detector module 200 and processing systems. For example, housing 220 may include openings for communications component 210 and for a power connector. Part or all of housing 220 may be light tight such that no ambient light is admitted to the interior of the housing. In various embodiments, housing 220 may include one or more elements or sections fabricated using injection or other molding techniques, 3D printing, laser cutting, or CNC milling. Materials used for housing 220 may include various plastics, metals, etc.

The front face of housing 220, that, when installed in gantry 104, is typically located facing specimen 112 in assembled PET scanner 100, can include one or more angled surfaces 224. PET detector module 200 may be mounted to a gantry 104 such that angled surface 224 is flush with an angled surface of an adjacent PET detector module 200. In this way, PET detector modules 200 may be arranged in ring, spherical, or other configurations. Housing 220 may have a shape that includes other features allowing PET detector modules 200 to be arranged in a tessellated or other configuration. The term "geometry," e.g., "scanner geometry" or "detector geometry" may indicate a configuration of PET detector modules to be used in an assembled PET scanner.

FIG. 3 shows an illustrative PET detector module 300, according to an embodiment. PET detector module 300 may include two SiPM array light detectors 304, 306. SiPM array light detectors 304,306 may use the components and/or configuration of SiPM array light detector 204 described with regard to FIG. 2. Crystal 202 may be located between the SiPM array light detectors 304, 306.

In the exemplary embodiment of FIG. 3, the PET detector module 300 may have spatial resolution in the range of 1.0 mm to 2.0 mm, such as 1.3 mm to 1.7 mm, e.g., 1.3 mm. Depth encoding may be, for example, in the range of 2 mm-3 mm, such as approximately 2 mm, e.g., 2 mm. Energy resolution may be, e.g., 21%. An exemplary imaging application for PET detector module 300 is imaging the rodent brain. PET detector module 300 may be used for a wide range of imaging applications, such as imaging the human wrist, foot, breast, brain, and vascular system; rodents; companion animals; primates; etc.

Crystal 202 of PET detector module 300 may be a crystal array with 20×20 elements. The crystal array may have a 1.0 mm crystal pitch. The crystal array may have a depth of 20 mm. The crystal array may have unpolished crystals. The crystals of the crystal array may be separated by diffuse reflector material. A white paper, e.g., a Toray reflector, may be used for the reflector material.

SiPM arrays 304, 306 of PET detector module 300 may each use 5×5 SiPM elements. Each SiPM element of SiPM arrays 304, 306 may be a 3×3 mm$^2$ blue-sensitive SiPM. The elements may be multiplexed using a resistive network. The two SiPM arrays 304, 306 may have a total of eight outputs, e.g., an output from each corner of each SiPM array. Event data including the outputs of SiPM arrays 304, 306 may be communicated to a processing system via communication component 210. The outputs may be decoded using Anger-type logic to yield the position within the crystal where a photon was detected.

In some embodiments, a PSPMT may be used in lieu of one of the SiPM arrays of PET detector module 300. The PSPMT may be, for example, a Hamamatsu C12 PSPMT. In this configuration, the PSPMT may be used for x- and y-positioning and the SiPM array may be used for z-positioning.

FIG. 4 shows an illustrative PET detector module 400, according to an embodiment. PET detector module 400 may include a single SiPM array light detector 404. SiPM array light detector 404 may use the components and/or configuration of SiPM array light detector 204 described with regard to FIG. 2.

In the exemplary embodiment of FIG. 4, the PET detector module 400 may have spatial resolution in the range of 3.0 mm to 4.0 mm, such as 3.0 mm to 3.5 mm, e.g., 3.0 mm. PET detector module 400 may include a first crystal array 402 and a second crystal array 403. Crystal array 402 may have 16×16 elements and crystal array 403 may have 15×15 elements. Crystal arrays 402 and 403 may be offset with respect to one another, e.g., half a crystal width in the x-direction and half a crystal width in the y-direction. Crystal arrays 402 and 403 may each have a depth of 10 mm. Crystal arrays 402 and 403 may each have a 3.0 mm crystal pitch. Crystal arrays 402 and 403 may have each have a depth of 10 mm. The crystal arrays may have polished crystals. The crystals of crystal arrays 402, 403 may be separated by reflector material, such as Teflon®, ESR, barium sulphate powder, etc. An exemplary imaging application for PET detector module 400 is imaging the equine limb.

SiPM array 404 of PET detector module 400 may use 6×6 SiPM elements. Each SiPM element of SiPM array 404 may be a 6×6 mm$^2$ SiPm, e.g., MicroFB-60035 SMT by SensL Ltd. The elements may be multiplexed using a resistive network. In another embodiment, SiPM array 404 may use an array of 8×8 SiPM elements. Each SiPM element of SiPM array 404 may be a 3×3 mm$^2$ blue-sensitive SiPm.

Event data including the outputs of SiPM array 404 may be communicated to a processing system via communication component 210. The outputs may be decoded using Anger-type logic to yield the x- and y-position within crystal arrays 402, 403 where a photon was detected. Determination of the z-position within crystal arrays 402, 403 where a photon was detected may be achieved by direct segmentation of flood histograms.

PET detector module 400 includes a power connector 424. Power connectors are described in detail with regard to FIG. 2.

Figure 5:
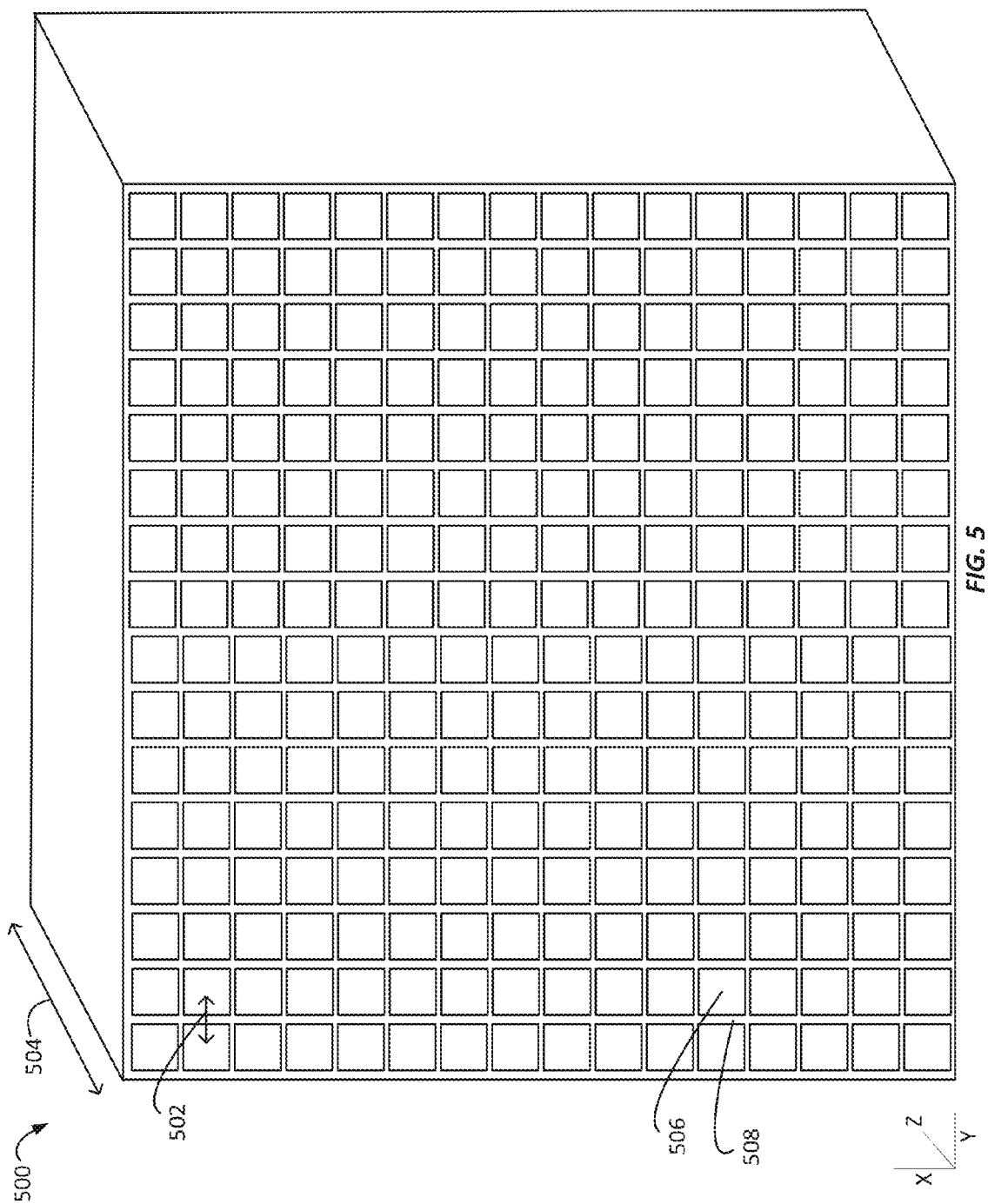
FIG. 5 shows an illustrative crystal array, according to an embodiment.

FIG. 5 is an illustrative crystal array 500, according to an embodiment. In some embodiments, crystal 202 may be a crystal array 500. Crystal array 500 is a 16×16 array of crystals. The crystal pitch is illustrated at 502. For example, the crystal pitch may be 0.5 mm. The depth of the crystal array is illustrated at 504. For example, the crystal depth may be 8 mm. Each crystal of the crystal array may be a 0.5 mm×0.5 mm crystal bar 506 with a length of 8 mm. Each crystal 506 of crystal array 500 may be separated from adjacent crystals by reflector 508, such as a white paper reflector.

PET Detector Module Case and Skin

In some embodiments, housing 220 for a PET detector module 102 may include a case and a skin. A PET detector module case may include one or more coupling features configured to mate with one or more coupling features of a PET detector module skin.

Figure 6A:
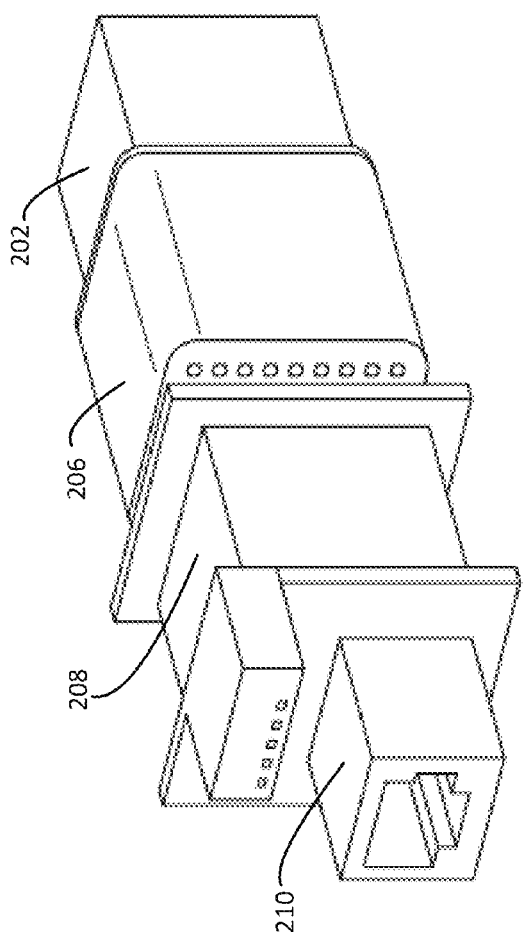
FIG. 6A shows illustrative components located on the interior of a case for a PET detector module, according to an embodiment.

FIG. 6A shows illustrative components of PET detector module 102 that may be located on the interior of a PET detector module case. In the illustrative example of FIG. 6A, crystal 202, a light detector (e.g., PSPMT 206), pre-amplifiers 208 and communication component 210 are shown, however, it will be recognized that any of the components of PET detector modules 200, 300, 400 may be located on the interior of a PET detector module case.

Figure 6B:
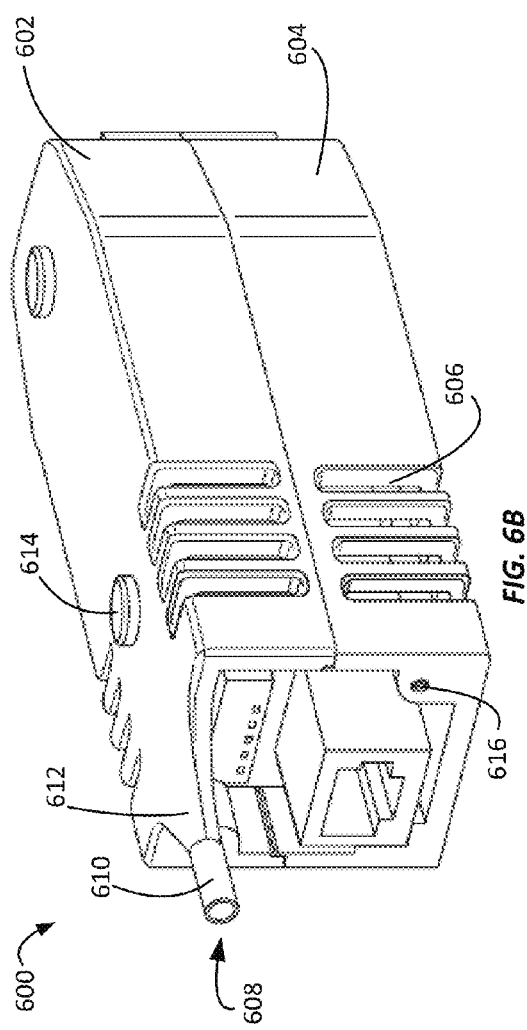
FIG. 6B shows an illustrative case for a PET detector module, according to an embodiment.

FIG. 6B shows an illustrative PET detector module case 600, according to an embodiment. In some embodiments, PET detector case 600 may partially or fully enclose one or more components of PET detector module 102 in a stable position such that the components are immobilized within the PET detector case. Using PET detector case 600 to hold the components of PET detector module 102 in fixed positions can allow PET detector module 102 to be transported, inserted into a PET detector skin, installed in a PET scanner system 100, adjusted relative to a gantry 104, etc., while preventing or minimizing shifting of the PET detector module components within the PET detector case 600.

PET detector module case 600 may include an upper case section 602 and a lower case section 604. In some embodiments, one or more components of PET detector module 102 may be placed within lower case section 604. Upper case section 602 may be placed on top of lower case section 604 to partially or fully contain the one or more components of PET detector module 102. In some embodiments, upper case section 602 may be movably coupled to lower case section 604, e.g., via a hinge.

In some embodiments, after upper case section 602 is placed on top of lower case section 604, upper case section 602 may be coupled to lower case section 604 by encircling upper case section 602 and lower case section 604 with a fastening device (not shown). The fastening device may be a removable device. For example, the fastening device may be heat shrink tubing and applying heat to the heat shrink tubing may cause the heat shrink tubing to shrink, causing upper case section 602 to be immovably coupled to upper case section 604. The heat shrink tubing may be cut away or otherwise removed from PET detector module case 600, allowing the components of PET module 102 to be adjusted, replaced, etc. PET detector module case 600 may include a recessed area for receiving heat shrink tubing, as described further below. Other means may be used to mechanically couple upper case section 602 to lower case section 604, such as adhesive, screws, etc.

It will be realized that other configurations for PET detector module case 600 may be used. For example, PET detector module case 600 may include a single element in lieu of upper case section 602 and lower case section 604. Upper case section 602 and lower case section 604 of PET detector module case 600 may have different shapes than shown. PET detector module case 600 may include more than two sections. In various embodiments, PET detector module case 600 may include one or more elements or sections fabricated using injection or other molding techniques, 3D printing, laser cutting, or CNC milling. Materials used for PET detector module case 600 may include various plastics, metals, etc.

PET detector module case 600 may include various features for heat management. For example, heat generated by preamplifiers 208 may need to be managed. PET detector module case 600 may include ventilation openings 606. Ventilation openings 606 are shown located in the vicinity of preamplifiers 208 to allow heat generated by preamplifiers 208 to escape PET detector module case 600 via ventilation openings 606. It will be recognized that alternative numbers, shapes, placements, and arrangements of ventilation openings may be used as needed for managing heat generated by components of PET detector module 102.

In some embodiments, PET detector module case 600 may include ventilation port 608. Ventilation port 608 may include a tubular section 610 and a manifold section 612. Air may be provided to ventilation port 608 for cooling one or more components of PET detector module 102. For example, temperature-controlled air, e.g., cooled air, may be directed to ventilation port 608 from an air supply via a channel such as a tube or duct that connects to ventilation port 608.

PET detector module case 600 may include one or more case guide elements 614. Case guide element 614 may mate with a corresponding feature of a device. For example, case guide element 614 may mate with a corresponding feature of a PET detector module skin used for coupling the PET detector module 600 to a surface. It may be desirable to use multiple case guide elements, such as the two case guide elements shown in FIG. 6B, to achieve a stable coupling between PET detector module 600 and a component to which the PET detector module is mechanically coupled. In some embodiments, case guide elements 614 may be projecting elements, such as the cylindrical pegs shown at 614. Case guide elements 614 may be integral components of a section or element of a PET detector module case 600. Alternatively, case guide elements 614 may be coupled to a section or element of PET detector module case 600 via adhesive, screws, or other coupling means.

PET detector module case 600 may include one or more features for preventing movement of the components of PET detector module 102 within PET detector module case 600. For example, PET detector module case 600 may include one or more holes 616. Each hole 616 may receive a screw, post, or other element that passes through hole 616 and comes into contact with a component of PET detector module 102, such as preamplifier 208 or a printed circuit board. When installed, the screw or other element may be fixed in place such that pressure is exerted on the component to prevent movement, e.g., along the longitudinal axis of the screw, of the components within the case. For example, a screw may pass through hole 616 and, when fully installed, the screw may exert pressure on preamplifier 208 to prevent movement of preamplifier 208 (and any components to which preamplifier 208 is mechanically coupled) within PET detector module case 600. Elements of PET detector module case 600 or hardware elements may be used in conjunction with the screw to immobilize the installed screw.

Any features discussed with regard to PET detector module case 600 may be incorporated into housing 220.

FIGS. 7A-7B show additional perspective views of PET detector module case 600, illustrating features of PET detector module case 600 according to various embodiments. In FIGS. 7A-7B, PET detector module case 600 includes guide elements 614 that are female connective elements, configured to mate with a male connective element of a PET detector skin or other device to which a PET detector module case 600 may be coupled.

In the illustrative embodiment of FIG. 7A, PET detector module case 600 includes a recessed area 702 for receiving heat shrink tubing 704, shown in FIG. 7B. Placing the heat shrink tubing 704 within recessed area 702 can reduce the probability of the heat shrink tubing moving relative to PET detector module case 600 after the heat shrink tubing has shrunk.

In some embodiments, PET detector module 102 may include a printed circuit board (PCB) 706. PET detector module case 600 may include one or more holes for receiving screws 708 that pass through PCB 706. The screws 708 that pass through PCB 706, when fully installed, may mechanically couple PCB 706 to PET detector module case 600, preventing PCB 706 (and components to which PCB 706 is mechanically coupled) from moving within PET detector module case 600.

PET detector module case 600 may include a visual reference 710, as shown in FIG. 7B. Visual reference 710 may include a protruding surface, labeled area, or other indicators for showing the location of a component of PET detector 102 within PET detector module case 600. For example, visual reference 710 can be used to indicate the location of crystal 202 within PET detector module case 600. Visual reference 710 can include information about a component of PET detector 102, such as description and/or visual indication of the width of crystal 202. In the illustrative example of FIG. 7B, visual reference 710 is a protruding surface of the end of PET detector module case 600. The protruding surface may be located adjacent to the position of crystal 202 within PET detector module case 600. Visual reference 710 may be located on the surface of PET detector module case 600 that, when PET detector module 102 is installed in PET scanner system 100, will face a specimen 112. The protruding surface may have an area corresponding to one or more dimensions of crystal 202. The protruding surface may include text and other indicators, such as an arrow, for indicating a dimension of crystal 202, such as a width of crystal 202.

Figure 8:
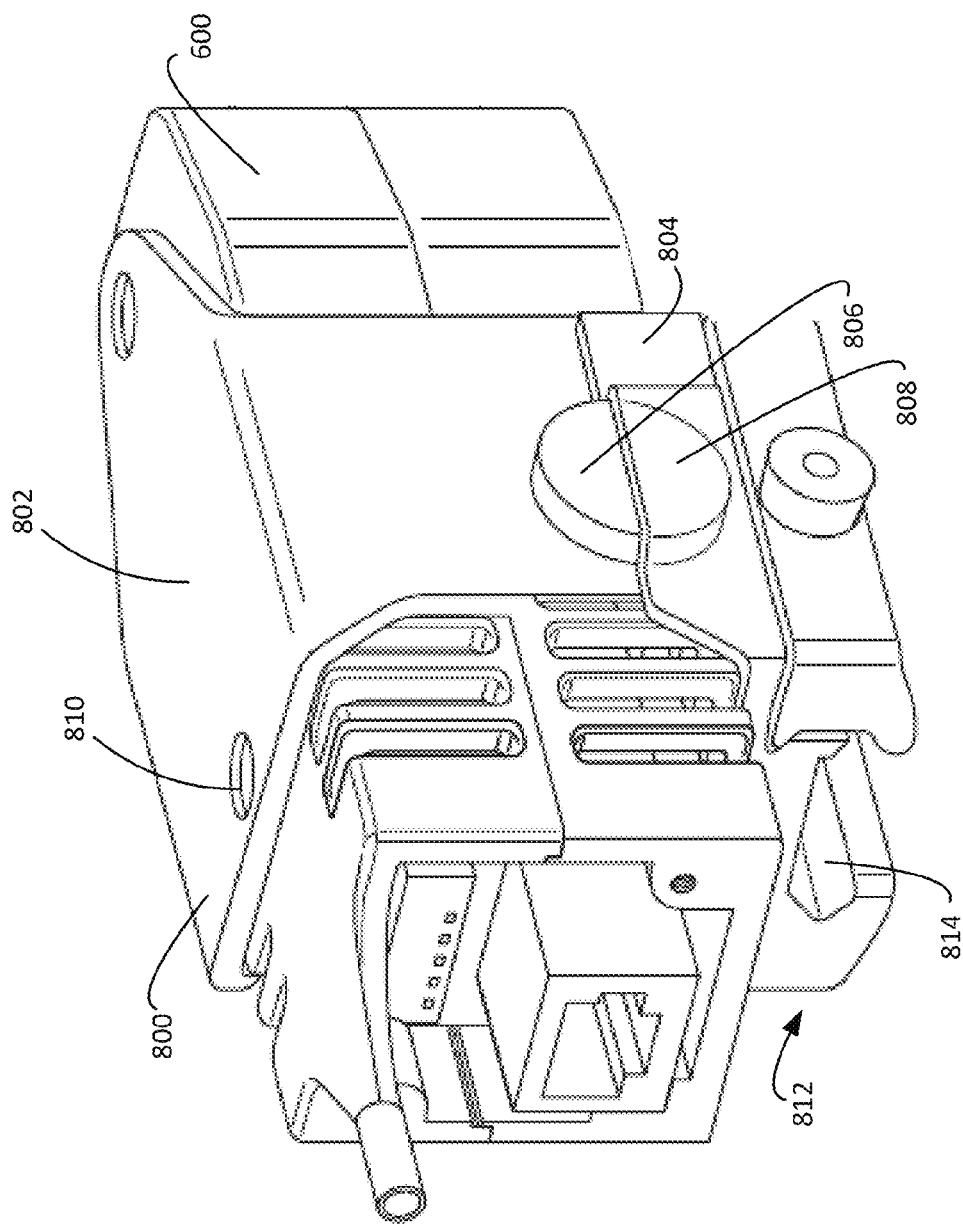
FIG. 8 shows an illustrative skin for a PET detector module, according to an embodiment.

FIG. 8 shows an illustrative PET detector module skin 800. PET detector module case 600 is shown inserted within PET detector module skin 800. PET detector skin 800 can include an upper skin section 802 and a lower skin section 804. PET detector skin 800 may be attached to a mounting surface, such as gantry 104. In some embodiments, PET detector module skins 800 are mounted to gantry 104 and PET detector modules 102 including PET detector module cases 600 can be subsequently inserted into PET detector module skins 800.

In some embodiments, upper skin section 802 may include a half cylinder protrusion 806 and lower skin section 804 may include a half cylinder protrusion 808. When upper skin section 802 is above lower skin section 804 such that half cylinder protrusion 806 abuts half cylinder protrusion 808, a fastening device (not shown) may be used to couple half cylinder protrusion 806 to half cylinder protrusion 808. The fastening device may be a removable device. For example, the fastening device may be a zip tie. The fastening device may be encircled about half cylinder protrusion 806 and half cylinder protrusion 808 to secure upper skin section 802 to lower skin section 804. Upper skin section 802 may be movably coupled to lower skin section 804, e.g., via a hinge. In some embodiments, half cylinder protrusions 806 and 808 may be located on two or more faces of the PET detector skin (e.g., located on the face shown and located on the opposite face of PET detector skin 800). It will be recognized that other attachment means may be used to couple upper skin section 802 to lower skin section 804.

It will be realized that other configurations for PET detector module skin 800 may be used. For example, PET detector skin may be a single element in lieu of upper skin section 802 and lower skin section 804. The sections 802, 804 of PET detector module skin 800 may have different shapes than shown. PET detector module skin 800 may include more than two sections. In various embodiments, PET detector skin 800 may include one or more elements or sections fabricated using injection or other molding techniques, 3D printing, laser cutting, or CNC milling. Materials used for PET detector skin 800 may include various plastics, metals, etc.

PET detector skin 800 may include one or more skin guide elements 810. Skin guide element 810 may mate with a corresponding case guide element of PET detector module case 600, such as case guide element 614. In some embodiments, skin guide element 810 is a hole or recessed area having a diameter that is slightly larger than the diameter of guide element 810, such that motion of PET detector case 600 relative to PET detector skin 800 is restricted when guide elements 614 are mated with case guide elements 810.

PET detector skin 800 may include a connective element 812 for mounting PET detector skin 800 to a surface, such as gantry 104. Connective element 812 may be a portion of lower skin section 804. Connective element 812 may be configured to receive a mounting component, such as a rail (e.g., a Picatinny rail, as described further below).

Connective element 812 may be integral component of a section or element of a PET detector module skin 800. Alternatively, connective element 812 may be coupled to a section or element of PET detector module skin 800, via adhesive, screws, or other coupling means. In some embodiments, connective element 812 may be a component of or attached to housing 220 or PET detector module case 600.

Connective element 812 may have a cross-sectional profile that includes an opening 814 for receiving a mounting component. For example, if a mounting element is a Picatinny rail, the connective element 812 may have a cross-sectional profile that includes an opening that matches the cross-sectional profile of the Picatinny rail. The opening 814 may be slightly larger than the cross-sectional profile of the Picatinny rail to allow the Picatinny rail to be received in the opening.

Figure 9A:
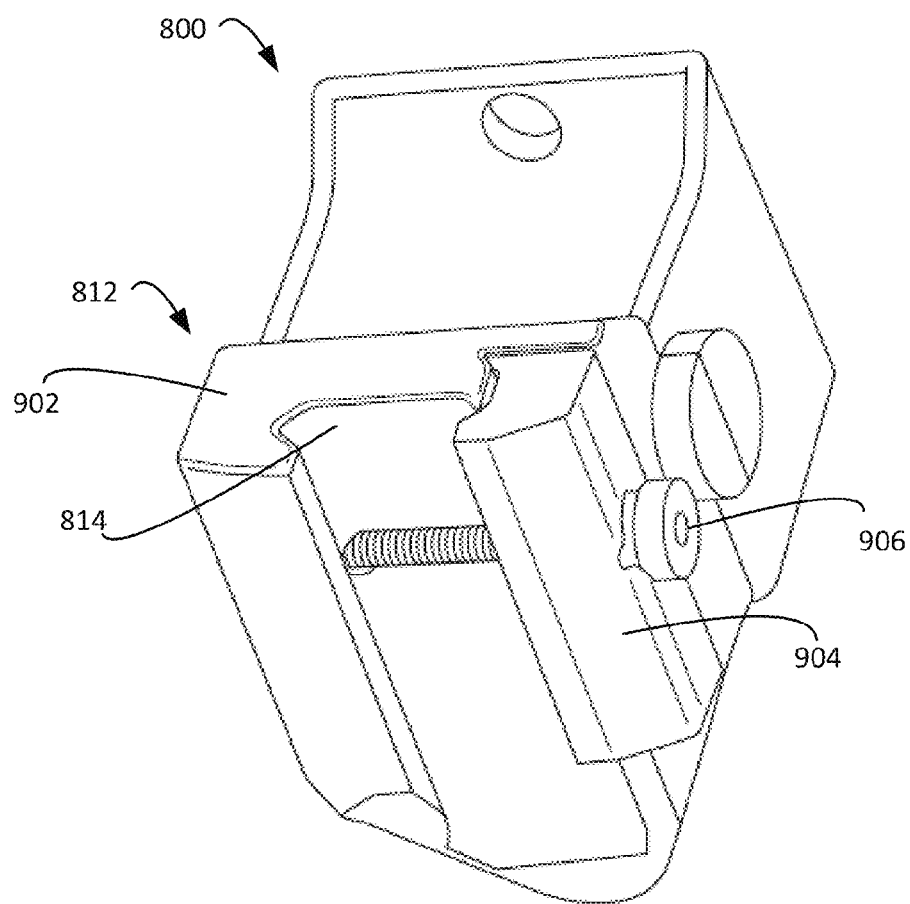
FIG. 9A shows a connective element, according to an embodiment.

FIG. 9A shows an illustrative connective element 812. Connective element 812 as shown in FIG. 9A includes elements of PET detector module skin 800. In some embodiments, connective element 812 may include elements of housing 202 or may be coupled to housing 202 or PET detector module case 600.

In some embodiments, connective element 812 may include a receiving component 902, a removable mounting bit 904 and a bolt 906. Receiving component 902 may include an opening for receiving a mounting component 950. The removable mounting bit 904 may couple to receiving component 902 using, e.g., a bolt 906. Receiving component 902 can be placed over a mounting component 950, such as Picatinny rail, and mounting bit 904 can be subsequently coupled to receiving component 902 using bolt 906 in order to couple PET detector skin 800 to the mounting component 950.

Figure 9B:
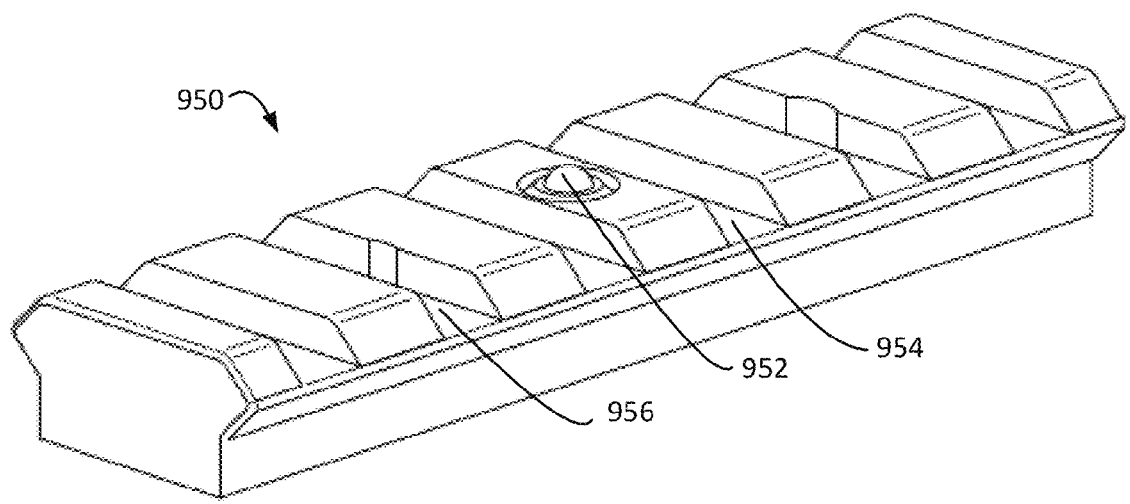
FIG. 9B shows an illustrative mounting element, according to an embodiment.

FIG. 9B shows an illustrative mounting component 950. Mounting component 950 may be a rail, such as a Picatinny rail (e.g. MIL-STD-1913). A Picatinny rail is a robust and accurate mechanism often used for mounting telescopic sights on firearms. Mounting component 950 may be coupled to a mounting surface, such as a gantry 104. For example, mounting component 950 may be coupled to gantry 104 via a connector or via multiple connectors (e.g., screws, bolts, or other connectors) at various locations along mounting component 950. In some embodiments, mounting component 950 may be removably coupled to gantry 104. PET detector module 600 may be stably coupled to gantry 104 by coupling connective element 812 to mounting component 950 and coupling mounting component 950 to gantry 104.

In some embodiments, mounting component 950 may include one or more motion restriction devices, such as grooves 954. When bolt 906 is used to secure mounting bit 904 to receiving component 902, bolt 906 may be seated in a groove 954 such that movement of PET detector skin 800 is restricted along the longitudinal axis of mounting component 950. When mounting bit 904 is secured to receiving component 902 such that mounting component 950 is partially surrounded by mounting bit 904 and receiving component 902, the motion of PET detector module 102 may be restricted along at least one axis. Fox example, the attachment of receiving component 902 and mounting bit 904 about the profile of mounting component 950 may restrict the motion of PET detector module skin 800 in the direction along the longitudinal axis of bolt 906. The attachment of receiving component 902 and mounting bit 904 about the profile of mounting component 950 may restrict the motion of PET detector module skin 800 in a direction that is perpendicular to the longitudinal axis of bolt 906 and perpendicular to the longitudinal axis of mounting device 950 (i.e., if the longitudinal axis of bolt 906 is an x-axis and the longitudinal axis of mounting device 950 is a y-axis, motion of PET detector module skin 800 relative to mounting component 950 is restricted along a z-axis.)

In some embodiments, an alternative motion restriction device, such as connector 952 may be used. Connector 952 may be, e.g., a ball plunger. The ball plunger may have a threaded housing, spring pressure, and other features for detachable and/or adjustable coupling. It will be recognized that alternative connector structures, such as a pin structure, may be used. Connector 952 may mate with a receiving portion, e.g., a recessed area, such as a half-spherical area, of connective element 812. When used with connector 952, connective element 812 may include one or more recessed areas in lieu of mounting bit 904 and bolt 906.

The attachment of connective element 812 to mounting component 950 may be adjusted such that bolt 906 is seated in different grooves 954 of mounting component 900. In this way, connective element 812 may be adjustably connected to mounting component 950 such that the position of PET detector module 102 may be adjusted relative to gantry 104 and/or specimen 112. For example, when connective element 812 is coupled to mounting component 950 with bolt 906 seated in a first groove 954, PET detector module may be located at a first position that is a first distance from specimen 112. When connective element 812 is coupled to mounting component 950 with bolt 906 seated in a second groove 956, PET detector module may be located at a second position that is a second distance from specimen 112. PET detector modules 102 is adjusted from the first position to the second position. At the first position and the second position, PET detector module 102 may be fixedly coupled to gantry 104 such that motion of PET detector module 102 relative to gantry 104 is restrained along one, two or three axes. It will be realized that alternative mounting components 950 and connective elements 812 may be used to adjustably mount a PET detector module 102 to gantry 104, such that motion of PET detector module 6102 relative to gantry 104 is restrained.

In some embodiments, connective element 812 may include construction components such as Lego®, Erector® set or other components that allow PET detector module 102 to be mounted to a gantry 104. For example, in lieu of connective element 812 and mounting element 950 as shown in FIGS. 9A-9B, PET detector module skin 800 may include a connective element 812 that includes female connective bits that allows the PET detector module skin 800 to be adjustably coupled to a mounting surface (e.g., a surface of gantry 104) that includes male connective bits (e.g., Lego® bits).

PET Scanner System Geometries

Figure 11:
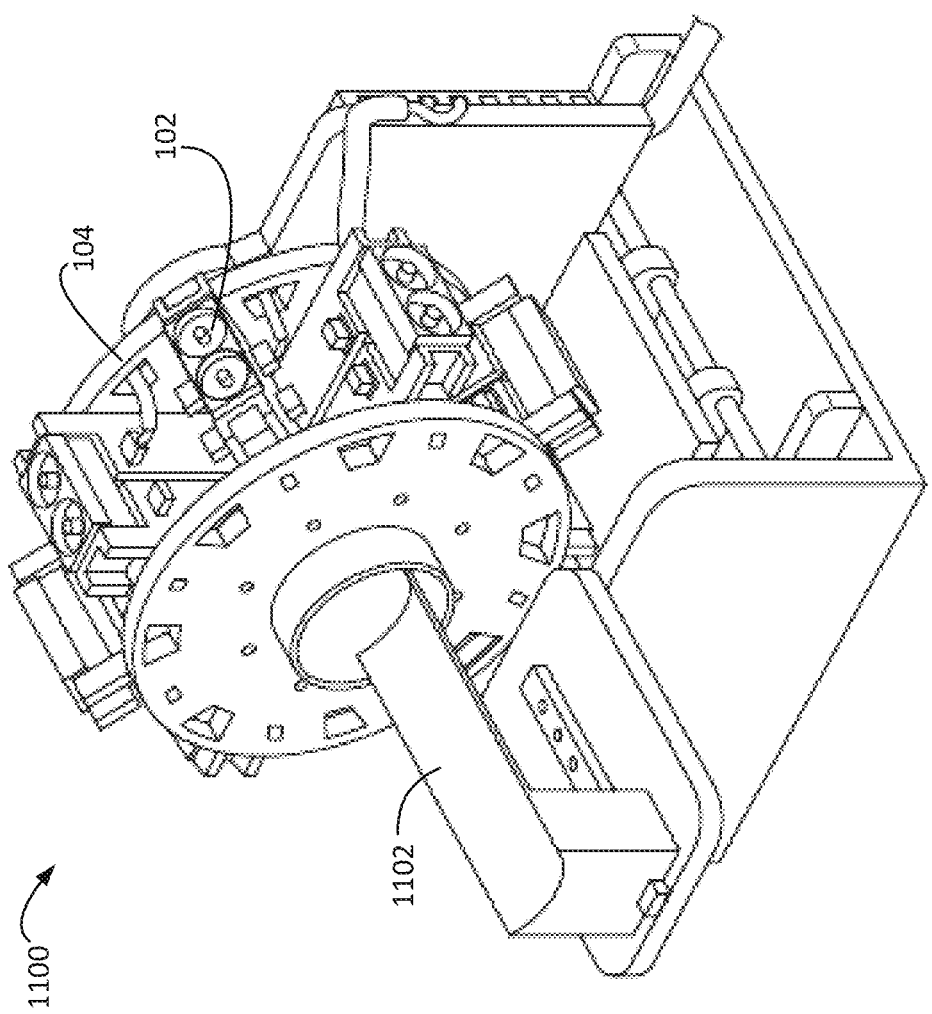
FIG. 11 shows an illustrative PET scanner system assembled from a modular PET kit, according to a second embodiment.
Figure 12:
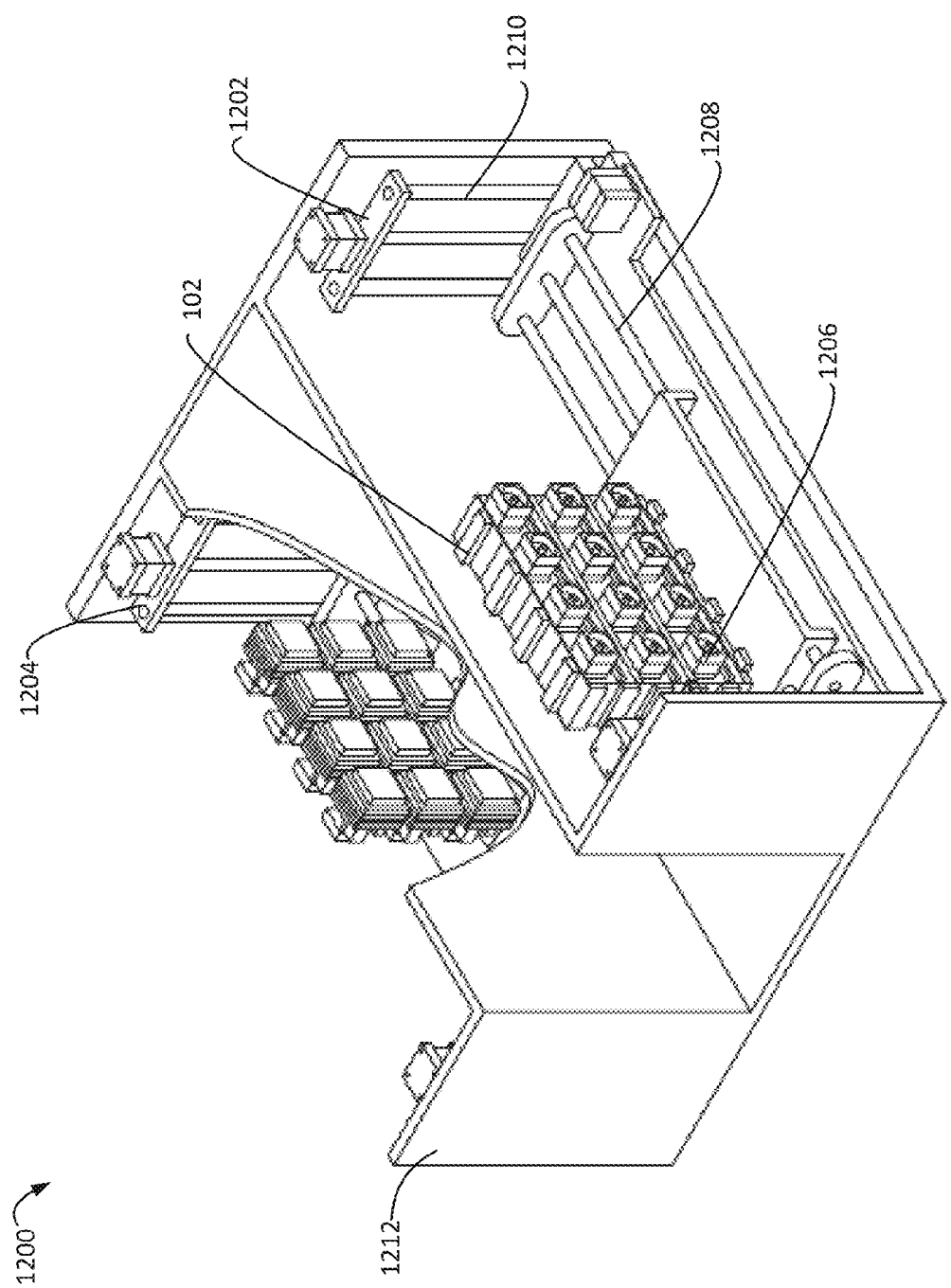
FIG. 12 shows an illustrative PET scanner system assembled from a modular PET kit, according to a third embodiment.

FIGS. 10-12 show illustrative PET scanner systems 1000, 1100, 1200 assembled from a modular PET kit, according to various embodiments. The modular PET kit can allow a user to construct various PET detector scanning configurations (i.e., geometries). For example, a user can mount PET detector modules 102 on a gantry 104 according to a geometry specific to a particular specimen to be analyzed. In some embodiments, one or more gantries 104 with various structures may be provided as components of a modular PET kit. Gantries 104 may be custom fabricated by a user to allow various geometries that are specific to particular scanning applications.

FIG. 10 shows an illustrative PET scanner system 1000. PET scanner system 1000 includes a plurality of PET detector modules 102 mounted to a gantry 104 in a circular geometry. PET scanner system 1000 may be configured to rotate e.g., if needed to reduce the impact of gaps between the detectors. For example, a scanner may rotate ⅛ of a turn about the axis that passes through the center of the ring of PET detector modules 102. In one embodiment, PET scanner 1000 may be used with PET detector modules 200, e.g., to produce a PET image of a specimen such as a human finger. The specimen may be located at the center of the ring of PET detector modules 102. The diameter of the ring of PET detector modules 102 and/or the number of PET detector modules 102 to be used in a PET scanner with the configuration shown for PET scanner system 1000 may be varied, e.g., to accommodate the size of the specimen to be scanned.

FIG. 11 shows an illustrative PET scanner system 1100. PET scanner system 1100 includes a plurality of PET detector modules 102 mounted to a gantry 104 in a circular geometry.

In PET scanner system 1100, two rings of PET detector modules 102 are shown. Each ring may include eight PET detector modules 102. PET scanner system 1100 may be configured to rotate e.g., if needed to reduce the impact of gaps between the detectors. For example, a scanner may rotate ⅛ of a turn about the axis that passes through the center of the rings of PET detector modules 102. In one embodiment, PET scanner 1100 may be used with PET detector modules 300, e.g., to produce a PET image of a specimen such as a rodent brain. During scanning, the specimen may be located at the center of the rings of PET detector modules 102. The diameter of the rings of PET detector modules 102 and/or the number of PET detector modules 102 to be used in a PET scanner with the configuration shown for PET scanner system 1100 may be varied, e.g., to accommodate the size of the specimen to be scanned.

Gantry 104 of PET scanner system 1100 may include table 1102. Table 1102 may be movable such that a specimen on table 1102 may be transported into the center of the rings of PET detector modules 102.

FIG. 12 shows an illustrative PET scanner system 1200. PET scanner system 1200 may include two detector plates 1206. An array of PET detector modules 102 may be mounted to each detector plate 1206. E.g., two arrays, each array including 3×4 PET detector modules, may be used. Detector plates 1206 of gantries 1202,1204 may be located across from one another with respect to a specimen. Detector plates 1206 can translate horizontally along rails 1208 (e.g., to image a larger area along a horizontal axis) and/or vertically along rails 1210 (e.g., to image a larger area along a vertical axis). Detector plates 1206 can move in tandem (e.g., to change the center of the field of view) or individually (e.g., in opposite directions to increase angular sampling.) Gantries 1202, 1204 may include motors for moving detector plates 1206.

In one embodiment, PET scanner 1200 may be used with PET detector modules 400, e.g., to produce a PET image of a specimen such as a limb of a standing horse. Gantries 1206, 1208 may including housing 1212 that provides protection of the PET detector modules 102 from the specimen. The number of PET detector modules 102 to be used in a PET scanner with the configuration shown for PET scanner system 1200 may be varied.

FIGS. 1 and 10-12 are illustrative of variations of PET scanner systems that may be assembled from a modular PET kit. It will be recognized that many additional scanner geometries and configurations may be realized with the components described herein. For example, a PET scanner including PET detector modules 102 arranged in a hemispherical or spherical geometry (e.g., surrounding or partially surrounding the specimen) may be assembled. In some embodiments, PET detector modules 102 may be moved (e.g., via robot control) for tracking the motion of a moving specimen. In other embodiments, a distal plane geometry can be created from two PET detectors that translate past each other. Another example of a geometry that may be assembled is a virtual pinhole geometry including at least one high-resolution PET detector and at least one low-resolution PET detector positioned across from one another relative to a specimen.

The modular PET kit may include one or more motion components. Motion components may include motors, actuators, sensors, relays, etc. The motion components may be coupled to one or more gantries and can cause PET detector modules to move with respect to a gantry. Motion control components may include control software and/or hardware. Motion control components may be local to a gantry and/or remote from a gantry. In some embodiments, signals received by a motion control component at a gantry from a processing system are used to control motion imparted by motion components.

The modular PET kit may also include a processing system. The processing system may include software and hardware. In some embodiments, the processing system may include an acquisition an control system, as described below.

Acquisition and Control System (ACS)

The processing system may include an event processing device, such as an acquisition and control system (ACS). The ACS may include one or more software modules configured to perform data acquisition, component control (such as PET detector module motion control), receiving user input, determining a system matrix based on a scanner geometry, determining coincidence events, generating PET images, etc. The ACS may further include one or more hardware components. The ACS may provide a user with an interface, such as a graphical user interface, to receive user input regarding PET detector configuration such that data from different detector types and various numbers of detectors can be processed.

Figure 13:
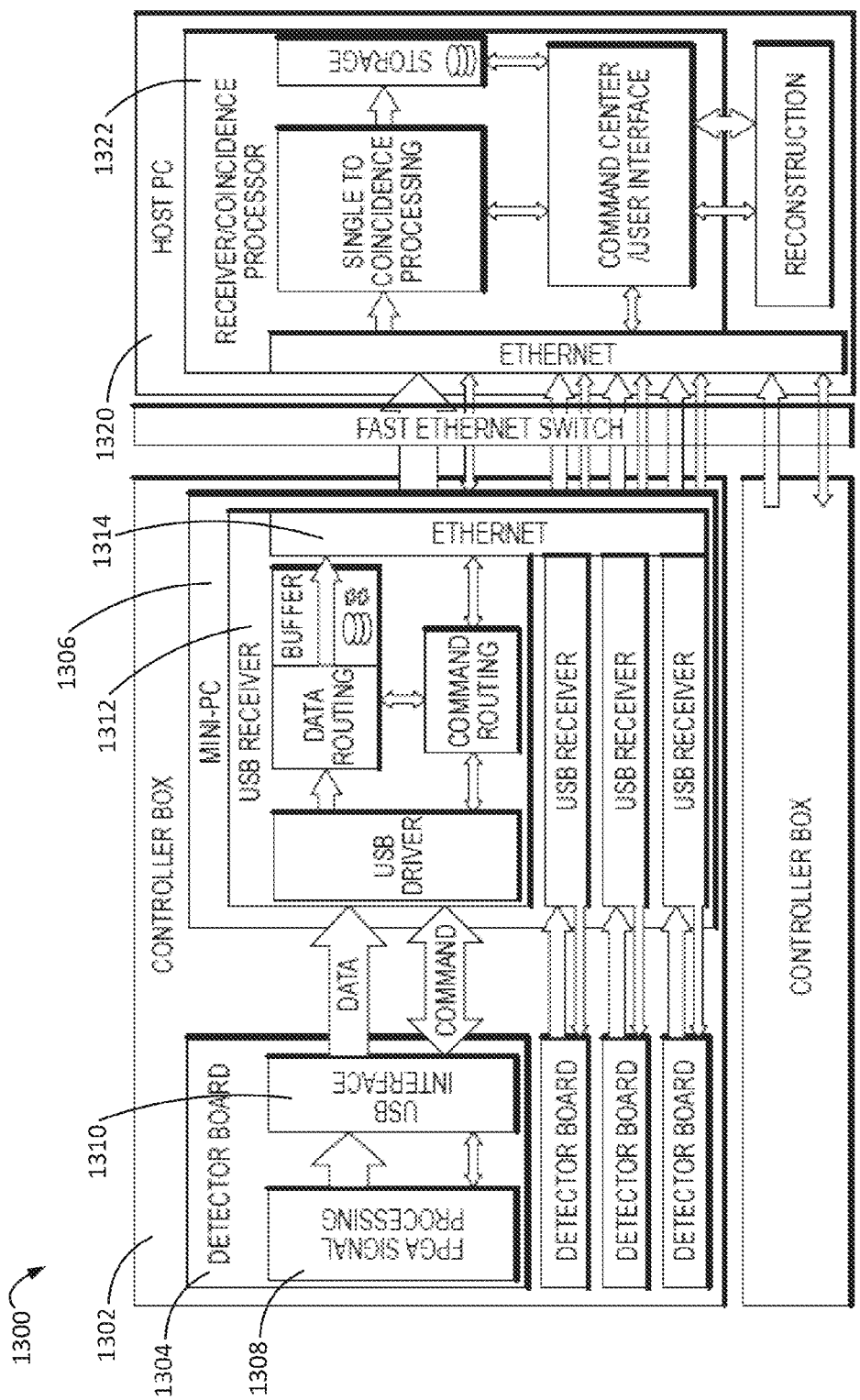
FIG. 13 shows an illustrative schematic for an acquisition and control system of a processing system, according to an embodiment.

FIG. 13 shows an illustrative schematic for ACS 1300, according to an embodiment. ACS may include a controller box 1302 and one or more computers, such as Host PC 1320.

Controller box 1302 may include one or more detector boards 1304 and a computer, such as Mini-PC 1306. For example, controller box 1302 may include four detector boards 1304. Mini-PC 1306 may be able to support up to four detector boards 1304.

Detector boards 1306 may receive event data from the PET detector modules 102. Each detector board 1304 may include an FPGA 1308 and a USB interface 1310. Detector board 1304 may include 4 inputs and 4 outputs. The inputs and outputs of detector board 1304 may be connected to FPGA 1308. Data received via inputs of FPGA 1308 (e.g., event data and other data received from PET detector modules 102) may be provided to Mini-PC 1306 via USB interface 1310. USB can provide payload data rates of up to 35 MB/s (USB2) or >350 MB/s (USB3), which may be sufficient to support multiple detectors (e.g., 4 detectors at a rate of 1.1 M or 11 M events per second each at 8 bytes per event). It will be recognized that where USB communications are described, alternative communication protocols, such as IEEE 1394 or other transfer protocols for communications between computers and peripheral devices, may be used.

Mini-PC 1306 may include one or more processors (e.g., Dual Atom processor), memory (e.g., 8 gigabytes of RAM), a hard drive (e.g., an SSD hard drive), and other components. Mini-PC 1306 may include a USB receiver 1312 for each detector board 1304 supported by the Mini-PC 1306. Mini-PC 1306 may include software for configuring detector boards. For example, the detector boards may be configured for PET detector module types 200, 300 and 400, depending on the type of PET detector module providing event data to the ACS.

USB receiver 1312 may buffer and/or store event data received from detector boards 1304. Event data received from detector boards 1304 may be routed by USB receiver 1312 to Host PC 1320 via an Ethernet interface 1314. USB receiver 1312 may provide commands to detector boards 1304. Control signals provided by USB receiver 1312 to a detector board 1304 may include, e.g., control signals to start/stop acquisition of data by the PET detector module 102, modify bias on light detectors (e.g., 204, 206), report status of PET detector module 102 (such as current temperature as determined by a temperature sensor), change speed of fan 218, configure the detector board, etc. Control signals from Mini-PC 1306 may be sent via FPGA 1308 of detector board 1304 to PET detector module 102.

Host PC 1320 may include one or more processors, memory, and other components. Host PC 1320 may support multiple controller boxes 1302. Host PC 1320 may include data acquisition control software to control one or more Mini-PCs 1306. In some embodiments, coincidence processing is performed by Host PC 1320. Host PC 1320 may receive and presort data received from USB receivers 1312, process single events to coincidence events, and store single and/or coincidence data for later processing. Using Host PC software for coincidence processing allows support of multiple PET scanner system configurations and geometries. The flexibility gained by software processing of single events at a later time allows for different energy and coincidence time windows or different random and scatter processing methods to be investigated using the same data set.

Software executed by Host PC 1320 may include coincidence processing module 1322. In some embodiments, a distributed computing architecture, such as a Hadoop architecture, is used for determining coincidence events. Coincidence events may be determined based on the timestamps of photon arrival events. The coincidence processing module may collect all events and use an algorithm to find matching pairs. For example, when photon arrival events fall within a predetermined time range, the events may be determined to be coincident events.

Host PC 1320 may include software for providing control signals to PET scanner systems (e.g., 100, 1000, 1100, 1200). For example, the control signals may include control signals to control motion of a gantry 104, a part of gantry 104, a surface on which a gantry 104 is mounted, or a specimen table 110.

The system described with respect to FIG. 13 can support single photon imaging, e.g., single photon emission computed tomography (SPECT).

Figure 14:
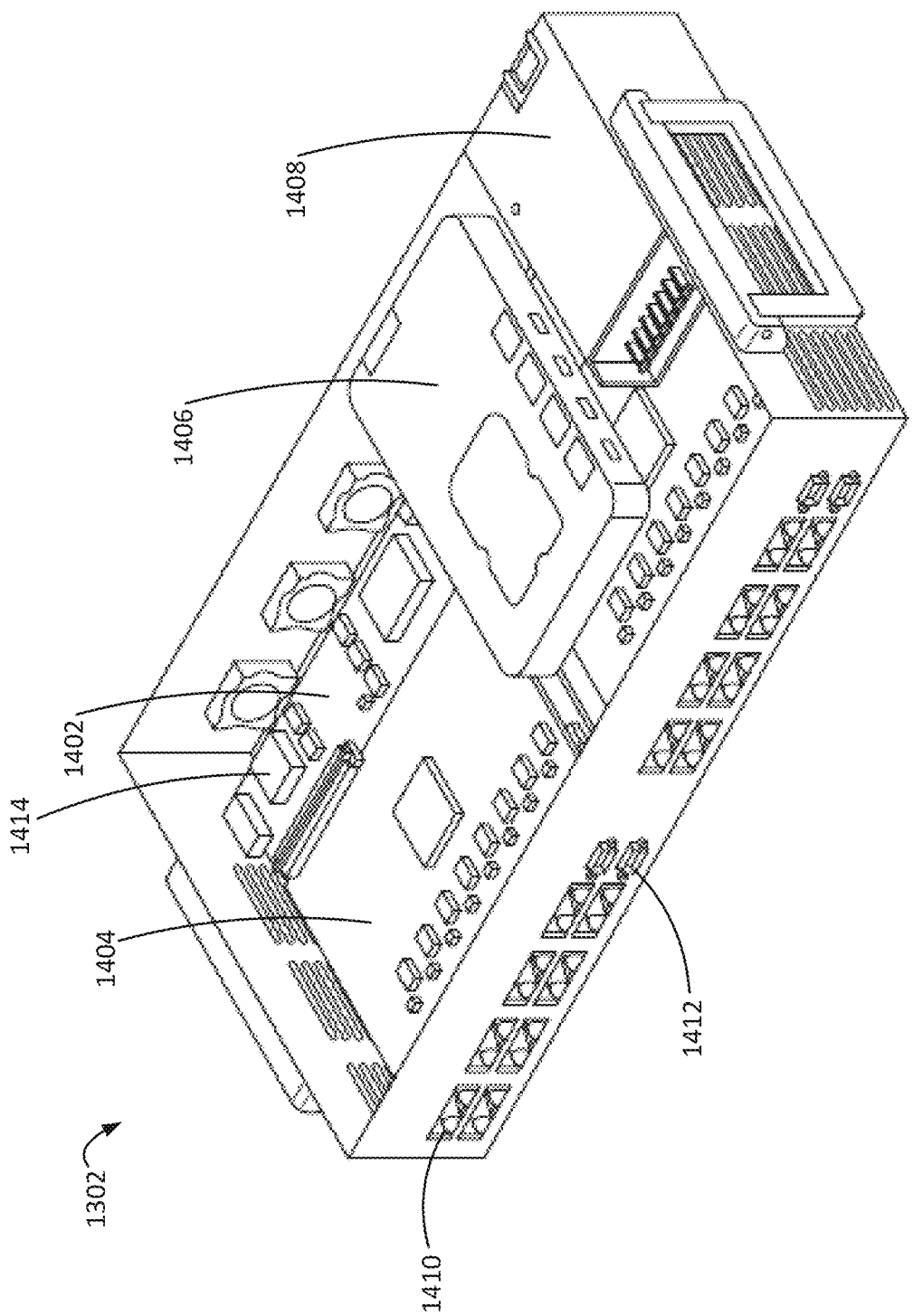
FIG. 14 shows an illustrative hardware layout for a controller box or an acquisition and control system, according to an embodiment.

FIG. 14 shows an illustrative hardware layout for a controller box 1302. While the illustrative controller box shown in FIG. 14 supports up to four detector boards, it will be recognized that the detector board controller box may support more or fewer detector boards in alternative embodiments. Controller box 1302 may include a USB and clock and interface board 1402, detector boards 1404, Mini-PC 1406, power supply 1408, PET detector module data ports 1410, gating and/or motor inputs 1412, and other components.

USB and Clock Interface Board 1402 may be a timing distribution board used to provide time synchronization of PET detector modules 102 to a desired accuracy, e.g., sub-nanosecond time synchronization. The timing distribution board may include a clock driver 1414 capable of providing a desired degree of accuracy of, for example, 100 picoseconds or better (e.g., MAX9153 by Maxim). The timing distribution circuit may be tested by measuring coincidence timing between two PET detector modules 102 using external test signals at the detector analog input.

Gating and/or motor inputs 1412 may receive data from event sensors, e.g., at gantry 104. Event sensors may include motion event sensors for recording motion events, such as gantry rotation, bed motion, subject motion, etc. Event sensors may include one or more biological event sensors for recording biological signals, such as cardiac, respiratory, or other events. Signals obtained by one or more of the motion event sensors and the biological event sensors may be inserted into the singles data stream (e.g., in the data sent from controller box 1302 to Host PC 1320) for processing.

Wireless PET Detector

Figure 15:
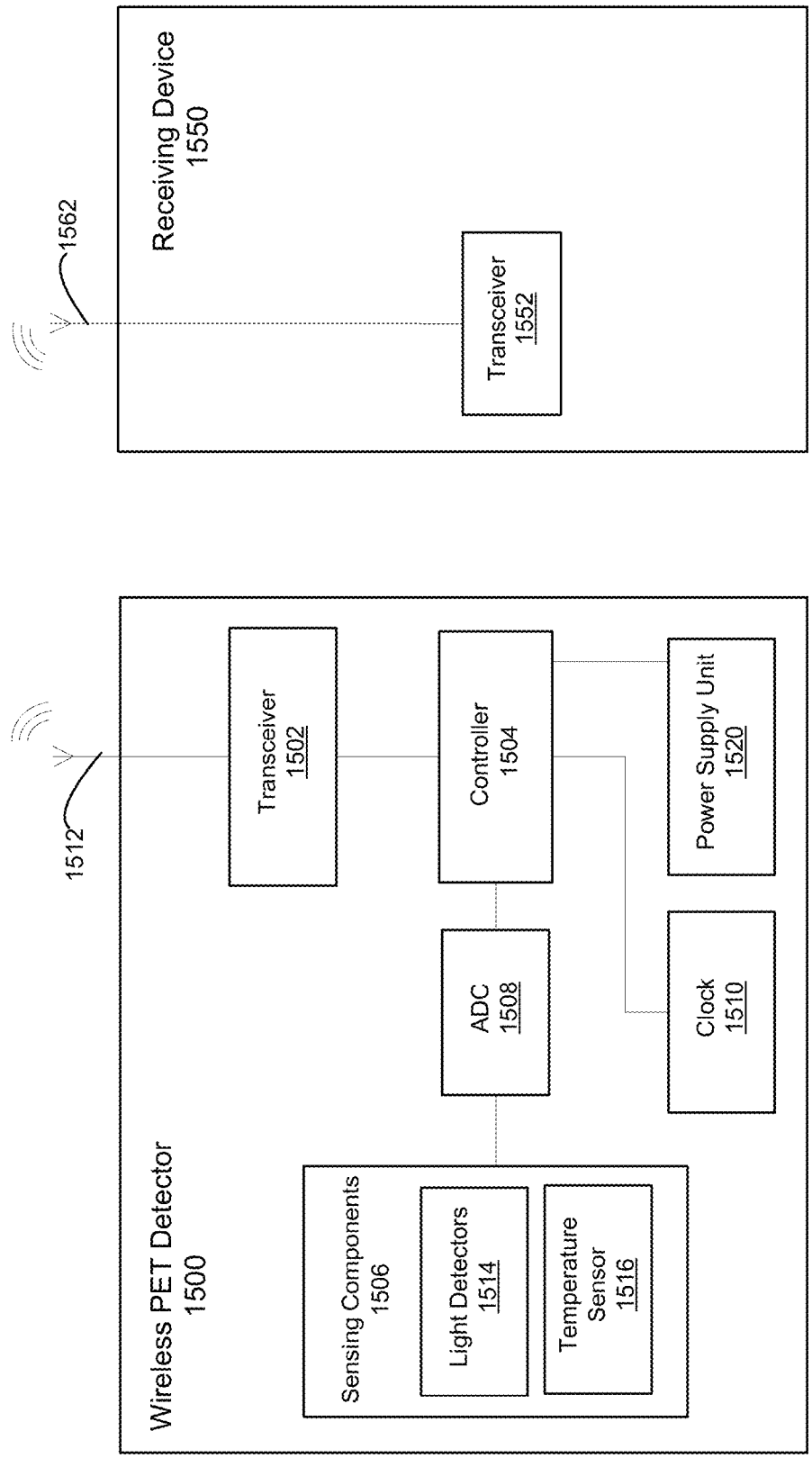
FIG. 15 shows an illustrative wireless PET detector and an illustrative receiving device, according to an embodiment.

FIG. 15 shows an illustrative wireless PET detector and an illustrative receiving device, according to an embodiment. PET detector modules 120 may transmit event data to a processing system, such as ACS 1300, via a wireless communication connection.

In some embodiments, PET detector module 120, 200, 300, 400 may be a wireless PET detector module, such as wireless PET detector module 1500. Wireless detector module 1500 can include a transceiver 1502, a controller 1504, sensing components 1506, analog-to-digital converter (ADC) 1508, clock 1510, and a power supply unit 1520. Various components of wireless PET detector 1500 may be connected to a printed circuit board (PCB), which may provide connections between components (e.g., traces).

Transceiver 1502 may include a transmitter element and a receiver element integrated into a single transceiver component. In some embodiments, a transmitter element and a receiver element are included in wireless PET detector 1500 as separate components for performing the operations described with reference to transceiver element 1502. Typically, transceiver 1502 is a radio frequency (RF) transmitter. Transceiver 1502 may transmit and/or receive data via an antenna 1512. Data, such as event data and any other communications with receiving device 500, may be transmitted from wireless PET detector 1500 using Wi-Fi, Bluetooth, or other wireless communication protocol.

Wireless PET detector 1500 may include a controller 1504 for controlling the components of wireless PET detector 1500. In some embodiments, controller 1504 is a field-programmable gate array (FPGA). Alternatively, controller 1504 may be a processor capable of executing instructions stored in memory. Controller 1504 may have on-board memory or may access a memory component of wireless PET detector 1500.

Sensing components 1506 may include sensors such as light detectors 1514 (e.g., light detectors 204, 206) and other sensors, such as temperature sensor 1516. Event data detected by light detectors 1516 of wireless PET detector module 1500 can be transmitted via transceiver 1502 to a transceiver 1552 of data receiving device 1550. The output of a temperature sensor 1516 may be transmitted via transceiver 1502 to a transceiver 1552 of data receiving device 1550.

In some embodiments, data for transmission from light detectors 1514, temperature sensor 1516, or other sensing components 1506 may be converted from analog data to digital data by ADC 1508 prior to transmission. Digital data may be sent from ADC 1508 to controller 1504. Controller 1504 may process the digital data from the ADC. For example, controller 1504 may format event data to be transmitted into an event word such that a timestamp, magnitude, and/or position for a single event are identifiable within the event word. Controller 504 may transmit the data via transceiver 1502 to a transceiver 1552 of receiving device 1550. In some embodiments, analog to digital conversion may be performed by controller 1504.

In some embodiments, a time-over-threshold approach may be used to generate event data. Because photon energy has a unique decay time, a magnitude of an event may be determined from the duration of time over which the photon energy is detected by light detectors 1514. Event data generated using the time-over-threshold approach can include the duration of time during which energy detected by light detector 1514 exceeds a threshold. When a time-over-threshold approach is used, wireless PET detector 1500 may include a comparator in lieu of an ADC. The comparator may determine when a magnitude of a signal generated by a light detector 1514 (corresponding to an energy level detected by the photodetector) exceeds a threshold. The output of the comparator may be provided to controller 1504 and transmitted via transceiver 1502 to a transceiver 1552 of receiving device 1550. By eliminating the need for an ADC, the power consumption of wireless PET detector 1500 may be reduced.

Wireless PET detector 1500 can include one or more clocks 1510. A clock 510 can be a component for generating a clock signal. Clock 1510 may be an element of controller 1504 or may be a separate component. Clock 1510 may be communicatively coupled to components of PET detector 1500 that use a clock signal. In some embodiments, a clock signal generated by clock 1510 may be used to determine a timestamp associated with an event.

Power supply unit 1520 may be a local power source for providing power to one or more components of wireless PET detector 1500. For example, power supply unit 1520 may be a battery.

In some embodiments, power may be provided to one or more components of wireless PET detector 1500 from a remote power source. For example, power may be received at power supply unit 1520 via a wired connection to a DC or AC power supply.

Receiving device 1550 can include a transceiver 1552. Receiving device 1550 may be an element of a processing system such as an element of controller box 1302, Mini-PC 1306, or Host PC 1320. Receiving device 1550 may receive event data from wireless PET detector 1500 via transceiver 1552. Mini-PC 1306 or Host PC 1320 may include software for receiving and analyzing event data received via transceiver 1552.

Transceiver 1552 may include a transmitter element and a receiver element integrated into a single transceiver component. In some embodiments, a transmitter element and a receiver element are included in receiving device 1550 as separate components for performing the operations described with reference to transceiver element 1552. Typically, transceiver 1552 is a radio frequency (RF) transmitter. Transceiver 1552 may transmit and/or receive data via an antenna 1562.

Synchronizing Wireless PET Detectors

As discussed above, in order to determine the position within a specimen where a pair of annihilation photons originated, the arrival time of photons at two PET detectors is determined. Because each wireless PET detector module 1500 may have its own clock 1510, the clock signals of multiple wireless PET detectors may drift with respect to one another. Because the clock signals may be used to determine event timestamps for photon arrival events, it may be necessary for the wireless PET detector clocks to be synchronized. Approaches to setting a reference time (e.g., a time t=0) are discussed below. A timestamp assigned to an event can be determined by a wireless PET detector 1500 based on a number of clock pulses that occur subsequent to the reference time.

In a first approach, a synchronization signal is received via wireless transceivers 1502 of wireless PET detectors 1500. For example, a specialized radio signal (e.g., a "chirp") may be generated by receiving device 1500 and transmitted to wireless PET detectors 1500 via transceiver 1552. Whereas wireless communication protocols such as Wi-Fi may not allow for synchronization with the requisite degree of accuracy, the specialized radio signal may be sent via wireless communications that do not use the Wi-Fi protocol. The synchronization signal may allow for a degree of accuracy required for PET event analysis, e.g., nanosecond-level or picosecond-level accuracy. When wireless PET detectors 1500 receive the chirp, the wireless PET detectors may set a clock pulse (e.g., a current high state, a current low state, a next high state, or a next low state) to a reference time (i.e., time t=0).

For example, each of the eight PET detector modules 102 shown in FIG. 10 may be wireless PET detectors 1500. The eight wireless PET detectors 1500 may each receive a chirp and, in response to receiving the chirp, assign a reference time t=0 to the next high state of their respective clocks 1510. The timestamps provided for events occurring at the wireless PET detectors 1500 can be determined using the number of clock pulses occurring subsequent to the reference time assigned in response to the received chirp.

In a second approach, a synchronization clock signal is provided to wireless PET detectors 1500. The synchronization clock signal may be provided from a remote power supply to wireless PET detectors 1500. In some embodiments, the synchronization clock signal may be an alternating current (AC) signal. For example, the synchronization clock signal may be an AC signal superimposed on a direct current (DC) signal provided from a remote power supply to wireless PET detectors 1500.

In one example, in response to a prompt signal (e.g., when a DC signal transitions from a low state to a high state), each PET detector 1500 determines when a transition of the AC signal from a low state to a high state occurs and sets a reference time t=0 based on the transition.

In some embodiments, an iterative approach to clock synchronization is used. For example, chirps may be periodically transmitted to wireless PET detectors 1500 at, e.g., one nanosecond intervals, one picosecond intervals, or other time interval. An iterative synchronization algorithm may be used to determine a reference time using, e.g., 10-100 chirps. Wireless PET detectors 1500 may communicate with the source of the synchronization signal and/or with other wireless PET detectors 1500 to accomplish synchronization. For example, wireless PET detectors 1500 may transmit a response chirp, e.g., at a particular number of clock pulses after a preliminarily determined reference time. In some embodiments, a handshaking process between wireless PET detectors 1500 and a synchronization signal source may occur.

Synchronization using the approaches described above may occur multiple times during analysis of a particular specimen.

PET Image Generation

Figure 16:
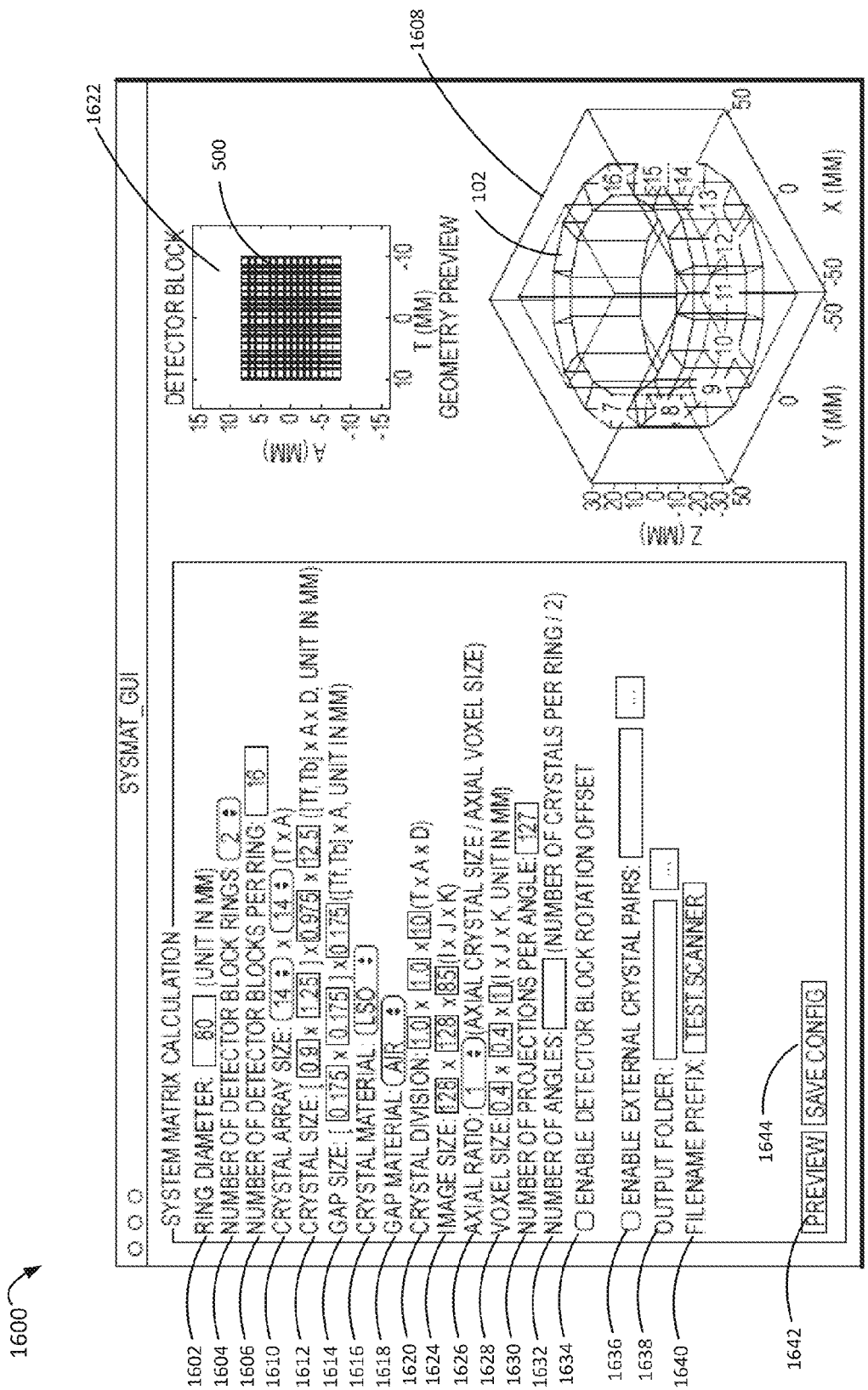
FIGS. 16-17 show illustrative screen shots of a graphical user interface, according to an embodiment.
Figure 17:
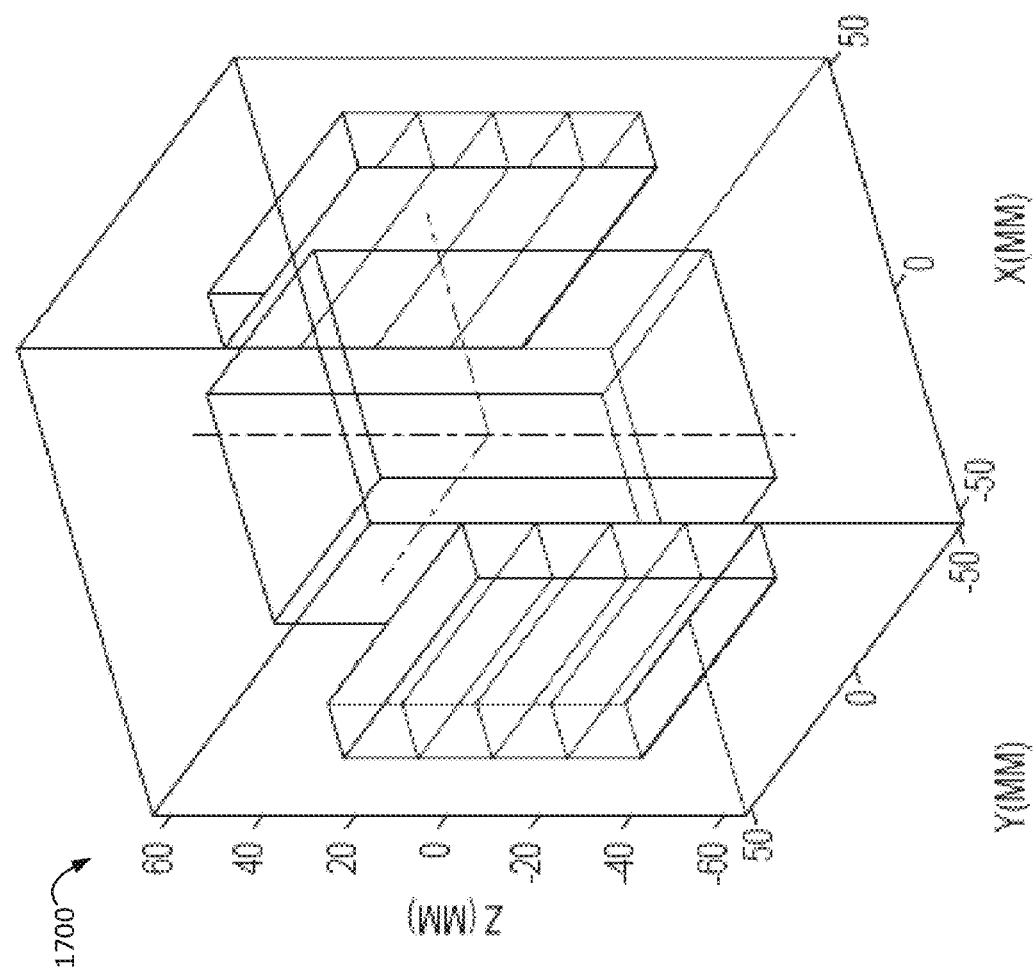

FIGS. 16-17 show illustrative screen shots of a user interface for indicating PET detector geometries. A graphical user interface (GUI), such as the user interface shown in FIGS. 16-17, can allow a user to indicate a geometry of the PET detector modules 102 of an assembled PET scanner system 100, 1000, 1100, 1200, etc.

FIG. 16 shows a screen shot 1600 of an illustrative GUI. The GUI may receive input from a user, e.g., via a selection of an option or typed input. The GUI may provide output to a user, e.g., by displaying an image of a PET scanner (or a part of a PET scanner) generated based on received input and/or based on a stored image. For example, the GUI may provide visual feedback of the scanner geometry by rendering the scanner, e.g., in two dimensions or in three dimensions. The GUI may be configured to allow a user to rotate the image for verification of the configuration. The GUI may display an image of a crystal generated based on received input and/or based on a stored image.

The GUI may allow a user to provide information to a processing system about the properties of a PET scanner 100. For example, a user may indicate a diameter of a ring of PET detector modules 102, as shown at 1602; a number of detector rings, as shown at 1604; and a number of PET detector modules 102 per ring, as shown at 1606. (PET detector module 102 may also be referred to as a "detector block," e.g., as used in screen shot 1600) An example of a PET scanner with two rings of PET detector modules is shown in FIG. 11. The GUI may generate an image of a ring of detectors, as indicated at 1608, based on information provided by a user at one or more of 1602-1606.

The GUI may allow a user to provide information to a processing system about the properties of a PET detector module 102. For example, a user may indicate a crystal array size, as shown at 1610; a crystal size, as shown at 1612; a gap size, as indicated at 1614; a crystal material, as shown at 1616; a gap material, as shown at 1618; and a crystal division, as indicated at 1620. The GUI may generate an image of a crystal array 500, as indicated at 1622, based on information provided by a user at one or more of 1610-1620.

The GUI may allow a user to provide information to a processing system about the rendering approach to be used by the processing system and/or about images to be produced by the processing system. For example, a user may indicate an image size, as shown at 1624; an axial ratio, as shown at 1626; a voxel size, as indicated at 1628; a number of projections per angle, as shown at 1630, and a number of angles, as shown at 1632.

The GUI may allow a user to provide additional information to a processing system. For example, a user may enable a rotation offset for PET detector modules 102, as shown at 1634; and enable external crystal pairs, as shown at 1636. A user may indicate an output folder (e.g., where input data, data associated with input data, and/or data generated based on the input data is to be stored), as indicated at 1638; and provide a filename prefix, as indicated at 1640. A user may select "Preview," as indicated at 1642, e.g., to direct the processing system to generate a PET scanner image, as shown at 1608, and/or a crystal array image, as shown at 1622. A user may select "Save," as indicated at 1644, e.g., to direct the processing system to store input data, data associated with input data, and/or data generated based on the input data.

FIG. 17 shows a screen shot 1700 of an illustrative GUI. Screen shot 1700 includes an image output of the GUI. The image may be, e.g., a preview image of a PET scanner. The PET scanner image shown in screen shot 1700 may be an image of the scanner geometry of PET scanner 1200.

Once the scanner geometry is defined, the GUI may generate a scanner configuration file. The configuration file may be used by reconstruction software to form a matrix, such as a sinogram blurring matrix. The configuration file may be used to relate the measured coincidence data to a geometric projection. In some embodiments, the processing system can generate system matrices for scanner models generated in the Geant4 Application for Emission Tomography (GATE) environment.

Based on the information received at the GUI, the processing system can create one or more matrices for a PET scanner. The one or more matrices may be transmitted to a reconstruction engine of the processing system. The processing system may use the one or more matrices in conjunction with data acquired by the PET detector modules to generate PET images. For example, the reconstruction engine may support 3D MAP and/or OSEM. The system matrices and generated PET images may be, e.g., 2-dimensional or three-dimensional images.

A combination of a simple geometric projection matrix and a sinogram blurring matrix may be used for modeling. Forward and back projectors may be implemented on a graphics processing unit (GPU). A system model may be factored to reduce the storage size of the factored model. For example, the storage size of the factored model may be about 2.5% of the accurate system model. Because of their relatively small size, in some embodiments, factored matrices may be loaded directly into memory of a CPU or a GPU.

Because a PET scanner assembled from a modular PET kit may comprise of a set of premade PET detector modules, each PET detector module may be pre-characterized using a single-photon response function (SPRF). The SPRF represents the probability of a photon that enters the detector module front face at position (x,y) and polar and azimuthal angles ($\phi,\theta$) being detected by a crystal 202 of a PET detector module 102. The SPRF can be computed analytically and/or measured using a collimated point source. For each PET detector module 102 (e.g., PET detector modules 200, 300, 400) in a modular PET kit, a full characterization of the SPRF may be generated and/or stored in a database of the processing system.

For a given geometry of any two PET detector modules in a PET scanner assembled from a modular PET kit, SPRFs may be used to form the coincidence response function for any ideal line projection based on the position and incidence angle of the line with respect to each detector module. For quick performance, the computation may involve only multiplications of the elements in the SPRFs. The result may be a sinogram blurring matrix that represents the probability of a pair of photons emitted along the line being detected by any PET detector pair. Using the SPRF, the geometric projection matrix and sinogram blurring matrix may be decoupled. The geometric projection matrix can be pre-computed or computed on-the-fly. Since geometric projection may model ideal line integrals, it can be performed independently of the detector configuration. In the case of limited angle tomography, geometric projection can be handled by setting ranges of the projection angle and radial bin. The sinogram blurring matrix can be formed on the fly using the pre-stored SPRFs based on a given scanner geometry. This approach can create an accurate system model quickly for different configurations. Geometric factors may be calculated based on the solid angle effect of coincidence photons, the scanner configuration, and known gaps between scintillation crystals and detector modules.

Figure 18:
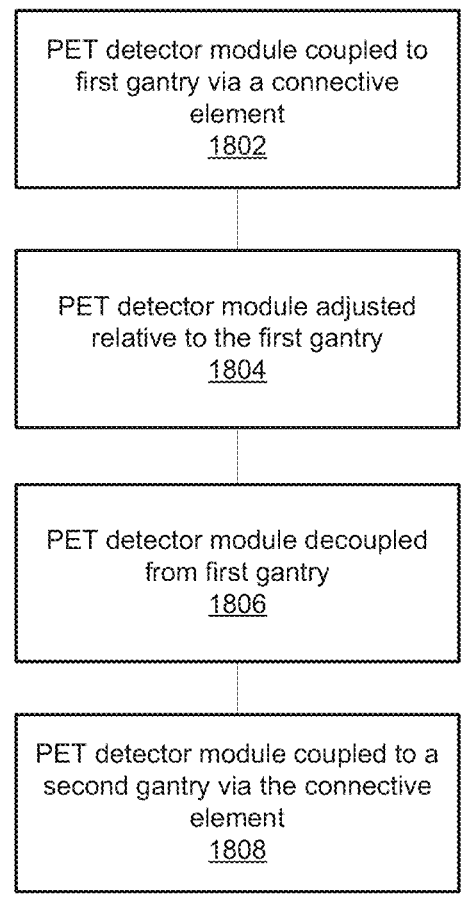
FIG. 18 shows an illustrative flow chart for assembling a PET scanner from a modular PET kit.

FIG. 18 is a flow diagram showing operations involved in assembling a PET scanner from a modular PET kit, according to an embodiment.

At operation 1802, a PET detector module 102 may be coupled to a first gantry 104 via a connective element 812. For example, a receiving component 902 of a connective element 812 may be placed such that an opening 814 of receiving component 902 receives a mounting component 950, such as a Picatinny rail. A mounting bit 904 may be coupled to receiving component 902 with a bolt 906.

In another embodiment, a connective element may be a Lego® block or part thereof coupled to housing 202. A Lego® block or part thereof may be coupled to a corresponding Lego® component coupled to first gantry 104.

In some embodiments, connective element 812 may be configured to allow PET detector module 102 to be coupled to a first gantry 104 without requiring the use of any tools.

At operation 1804, the PET detector module 102 may be adjusted relative to the first gantry 104. For example, bolt 906 may be moved from a first groove 954 of mounting component 950 to a second groove 956 of mounting component 950, such that PET detector module 102 is located to closer to of further away from a position where specimen 112 will be located when the PET scanner system 100 is operative.

At operation 1806, the PET detector module 102 may be decoupled from first gantry 104. For example, bolt 906 may be removed from mounting bit 904 such that mounting bit 904 can be disconnected from receiving component 902 and mounting component 950. PET detector module 102 may then be disconnected from first gantry 104.

At operation 1808, the PET detector module 102 may be coupled to a second gantry. The second gantry may have a different structure and/or geometry of PET detector modules 102 from the structure and/or geometry of PET detector modules 102 of the first gantry.

Figure 19:
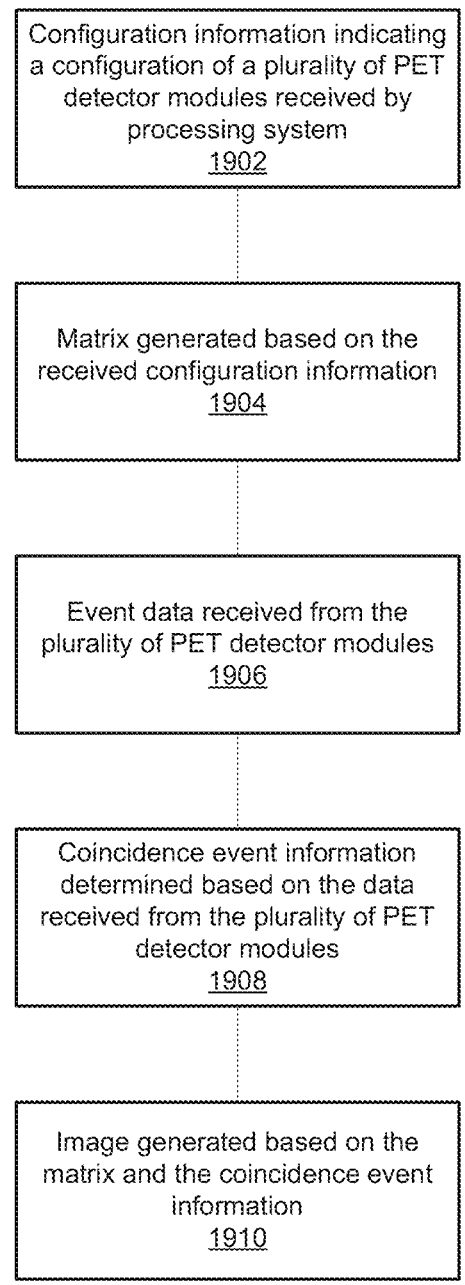
FIG. 19 shows an illustrative flow chart for generating an image using data from a plurality of PET detector modules.

FIG. 19 is a flow diagram showing operations involved in generating an image using data from a plurality of PET detector modules.

At operation 1902, configuration information indicating the configuration of a plurality of PET detector modules 102 may be received by a processing system. For example, a user may provide configuration information to the processing system via a GUI as described with regard to FIGS. 16 and 17. The configuration information may be stored by a storage device of the processing system.

At operation 1904, a matrix may be generated based on the received configuration information. For example, the processing system may determine a system matrix for the scanner geometry defined via the GUI. In another embodiment, a previously stored matrix may be selected or determined. The matrix may be provided to an ACS 1300.

At operation 1906, the processing system may receive event data from the plurality of PET detector modules 102. For example, controller box 1302 of ACS 1300 may receive event data from PET detector modules 102 at detector boards 1304. Mini-PC 1306 of controller box 1302 may receive the event data from detector boards 1304 via, e.g., a USB connection. Mini-PC 1306 may transmit the event data to Host PC 1320 via, e.g., an Ethernet connection.

At operation 1908, the processing system may determine coincidence event information using the received event data. For example, Host PC 1320 may use a coincidence processing software module to determine coincidence events based on single event data received from Mini-PC 1306.

At operation 1910, the processing system may generate an image using the matrix and the coincidence event information. For example, Host PC 1320 or another device of the processing system may use a reconstruction engine to perform MAP reconstruction in order to generate a PET image.

Computer System

The various participants and elements described herein may operate one or more computer apparatuses to facilitate the functions described herein. Any of the elements described herein, including any servers, processors, or databases, may use any suitable number of subsystems to facilitate the functions described herein.

Figure 20:
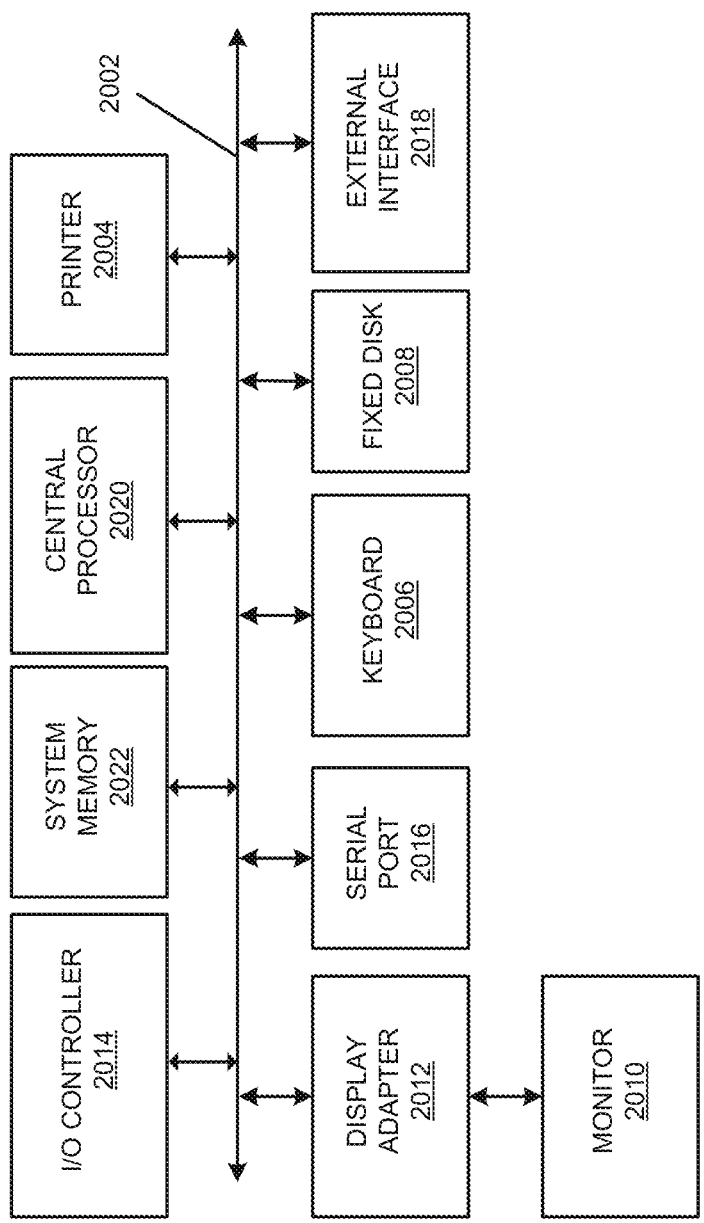
FIG. 20 shows a block diagram of an illustrative computing system, according to an embodiment.

Examples of such subsystems or components are shown in FIG. 20. The subsystems shown in FIG. 20 may be interconnected via a system bus 2002. Additional subsystems such as a printer 2004, keyboard 2006, fixed disk 2008 (or other memory comprising computer readable media), monitor 2010, which may be coupled to display adapter 2012, and others are shown. Peripherals and input/output (I/O) devices, which may couple to I/O controller 2014 (which can be a processor or other suitable controller), can be connected to the computer system by any number of means known in the art, such as serial port 2016. For example, serial port 2016 or external interface 2018 can be used to connect the computer apparatus to a wide area network such as the Internet, a mouse input device, or a scanner. The interconnection via system bus allows the central processor 2020 to communicate with each subsystem and to control the execution of instructions from system memory 2022 or the fixed disk 2008, as well as the exchange of information between subsystems. The system memory 2022 and/or the fixed disk 2008 may embody a computer readable medium.

Embodiments of the technology are not limited to the above-described embodiments. The specific details of the specific aspects may be combined in any suitable manner without departing from the spirit and scope of embodiments of the technology.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A positron emission tomography (PET) detector module for connection to a gantry, comprising:
    a housing that includes one or more connective elements configured to removably and adjustably couple the PET detector module to the gantry;
    only one crystal located within the housing;
    at least one light detector configured to detect light emitted by the crystal; and
    a communication component configured to communicate data from the at least one light detector to an event processing device.

2. The PET detector module of claim 1, further comprising:
    a heat control module that includes at least one of a temperature sensor, a fan, a peltier, a heat sink, a heat pipe, and an airflow manifold.

3. The PET detector module of claim 1, wherein the PET detector module housing includes a case and a skin, wherein the case includes at least one guide element to mate with a guide element of the skin, and wherein the skin includes the at least one connective element.

4. The PET detector module of claim 1, wherein each of the one or more connective elements has a cross-sectional profile including an opening to receive a rail coupled to the gantry.

5. The PET detector module of claim 4, wherein the rail includes a plurality of grooves configured to receive a portion of the connective element.

6. The PET detector module of claim 5, wherein the plurality of grooves comprises a first groove and a second groove; the first groove is configured so that when the portion of the connective element is received by the first groove of the plurality of grooves, the PET detector module is located at a first distance from a specimen, and the second groove is configured so that when the portion of the connective element is received by the second groove of the plurality of grooves, the PET detector module is located at a second distance from the specimen, wherein the first distance is greater than the second distance.

7. The PET detector module of claim 1, wherein the at least one light detector includes:
a silicon photomultiplier (SiPM) adjacent to a first face of the crystal, and
a position sensitive photo-multiplier tube (PSPMT) adjacent to a second face of the crystal, wherein the first face of the crystal is opposite the second face of the crystal.

8. The PET detector module of claim 1, wherein the at least one light detector includes:
a first silicon photomultiplier (SiPM) array adjacent to a first face of the crystal, and
a second silicon photomultiplier (SiPM) array adjacent to a second face of the crystal, wherein the first face of the crystal is opposite the second face of the crystal.

9. The PET detector module of claim 1, wherein an indicator on the exterior of the housing provides information about the location of the crystal.

10. The PET detector module of claim 1, wherein the communication component includes a jack configured to removably couple with a data cable, wherein the PET detector module is configured to transmit data via the data cable when the data cable is coupled with the jack.

11. The PET detector module of claim 1, wherein the communication component includes at least one of a wireless transmitter, a wireless receiver, and a wireless transceiver.

12. A positron emission tomography (PET) detector kit comprising:
a first gantry;
a plurality of PET detector modules, wherein each of the plurality of PET detector modules includes:
a housing that includes at least one connective element configured to removably and adjustably couple the PET detector module to the first gantry,
only one crystal located within the housing,
at least one light detector configured to detect light emitted by the crystal, and
a communication component configured to communicate data from the at least one light detector to an event processing device; and
the event processing device including
at least one processor; and
one or more non-transitory computer-readable storage media containing instructions configured to cause the one or more processors to perform operations including:
receiving data from the plurality of PET detector modules, and
determining coincidence events based on the received data.

13. The PET detector kit of claim 12, further comprising a second gantry, wherein the at least one connective element is configured to removably and adjustably couple the PET detector module to the second gantry.

14. The PET detector kit of claim 12, wherein the operations further include receiving a matrix, wherein the matrix is determined from configuration information indicating a configuration of the plurality of PET detector modules.

15. The PET detector kit of claim 14, wherein the configuration information is received by the event processing device via a graphical user interface.

16. The PET detector kit of claim 14, wherein the configuration information includes at least one of a number of PET detector modules, a ring diameter, a number of rings; a crystal size; and a crystal material.

17. The PET detector kit of claim 14, wherein the operations further include generating an image, wherein the image is based on the matrix and the coincidence events.

18. The PET detector kit of claim 12, wherein the event processing device further includes a clock device, wherein the operations further include transmitting a synchronization signal from the clock device to the plurality of PET detector modules.

19. The PET detector kit of claim 18, wherein the synchronization signal is superimposed on a power signal provided from the event processing device to the plurality of PET detector modules.

20. A method comprising:
coupling, via at least one connective element, a PET detector module to a first gantry, wherein the PET detector module includes:
a housing that includes the least one connective element,
only one crystal located within the housing,
at least one light detector configured to detect light emitted by the crystal, and
a communication component configured to communicate data from the at least one light detector to an event processing device;
adjusting, via the least one connective element, a position of the PET detector module relative to the first gantry; and
decoupling the PET detector module from the first gantry.

21. The method of claim 20, further comprising coupling, via the at least one connective element, the PET detector module to a second gantry.

* * * * *